(12) United States Patent
Ishida et al.

(10) Patent No.: US 11,298,508 B2
(45) Date of Patent: Apr. 12, 2022

(54) CATHETER ASSEMBLY

(71) Applicant: TERUMO KABUSHIKI KAISHA, Tokyo (JP)

(72) Inventors: Masahiro Ishida, Kanagawa (JP); Yasunobu Zushi, Yamanashi (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 152 days.

(21) Appl. No.: 16/577,199

(22) Filed: Sep. 20, 2019

(65) Prior Publication Data
US 2020/0023167 A1 Jan. 23, 2020

Related U.S. Application Data

(63) Continuation of application No. PCT/JP2018/012177, filed on Mar. 26, 2018.

(30) Foreign Application Priority Data

Mar. 27, 2017 (JP) .............................. JP2017-060706

(51) Int. Cl.
*A61M 25/06* (2006.01)
*A61M 25/00* (2006.01)

(52) U.S. Cl.
CPC .... *A61M 25/0612* (2013.01); *A61M 25/0068* (2013.01); *A61M 25/0097* (2013.01)

(58) Field of Classification Search
CPC .......... A61M 25/0643; A61M 25/0612; A61M 25/0068; A61M 25/0097; A61M 25/0606;
(Continued)

(56) References Cited

U.S. PATENT DOCUMENTS 4,652,256 A * 3/1987 Vaillancourt ...... A61M 25/0111
604/168.01
5,009,642 A * 4/1991 Sahi .................. A61M 25/0643
604/158
(Continued)

FOREIGN PATENT DOCUMENTS

JP 2015-047493 3/2015
JP 2016-221231 A 12/2016
(Continued)

OTHER PUBLICATIONS

International Search Report for International Application No. PCT/JP2018/012177, dated Jun. 26, 2018.
(Continued)

*Primary Examiner* — Bhisma Mehta
*Assistant Examiner* — Robert F Allen
(74) *Attorney, Agent, or Firm* — Thaine Lennox-Gentle; Sheridan Ross, PC

(57) ABSTRACT

A catheter assembly includes a catheter, a catheter hub, an inner needle, and an inner needle hub. The catheter assembly is disposed in a hollow portion axially extending in the interior of the inner needle, and includes a blunt needle having a distal end portion blunter than a needle tip and a movement mechanism for moving the blunt needle. The movement mechanism is configured separately from the catheter hub and causes the distal end of the blunt needle to protrude beyond the needle tip along with the movement of the catheter.

18 Claims, 20 Drawing Sheets

(58) Field of Classification Search
CPC ..... A61M 25/0618; A61B 2017/22042; A61B 2017/22038
See application file for complete search history.

(56) References Cited

U.S. PATENT DOCUMENTS

| | | | |
|---|---|---|---|
| 8,932,258 B2* | 1/2015 | Blanchard | A61M 25/0105 604/164.08 |
| 2001/0018572 A1* | 8/2001 | Kinsey | A61M 25/0643 604/164.06 |
| 2004/0073141 A1* | 4/2004 | Hartley | A61M 25/09033 600/585 |
| 2015/0231364 A1* | 8/2015 | Blanchard | A61M 25/09041 604/164.08 |
| 2016/0331938 A1* | 11/2016 | Blanchard | A61M 25/0618 |
| 2017/0028172 A1 | 2/2017 | Ishida | |
| 2017/0043132 A1 | 2/2017 | Ishida | |

FOREIGN PATENT DOCUMENTS

| | | |
|---|---|---|
| WO | WO 2016/185909 A1 | 11/2016 |
| WO | WO 2016/185950 A1 | 11/2016 |
| WO | WO 2016/187063 A1 | 11/2016 |
| WO | WO 2016/152415 A1 | 9/2019 |

OTHER PUBLICATIONS

Written Opinion for International Application No. PCT/JP2018/012177, dated Jun. 26, 2018.
Extended Search Report for European Application No. 18774726.6, dated Dec. 18, 2020.
International Preliminary Report on Patentability for International Application No. PCT/JP2018/012177, dated Oct. 10, 2019.

* cited by examiner

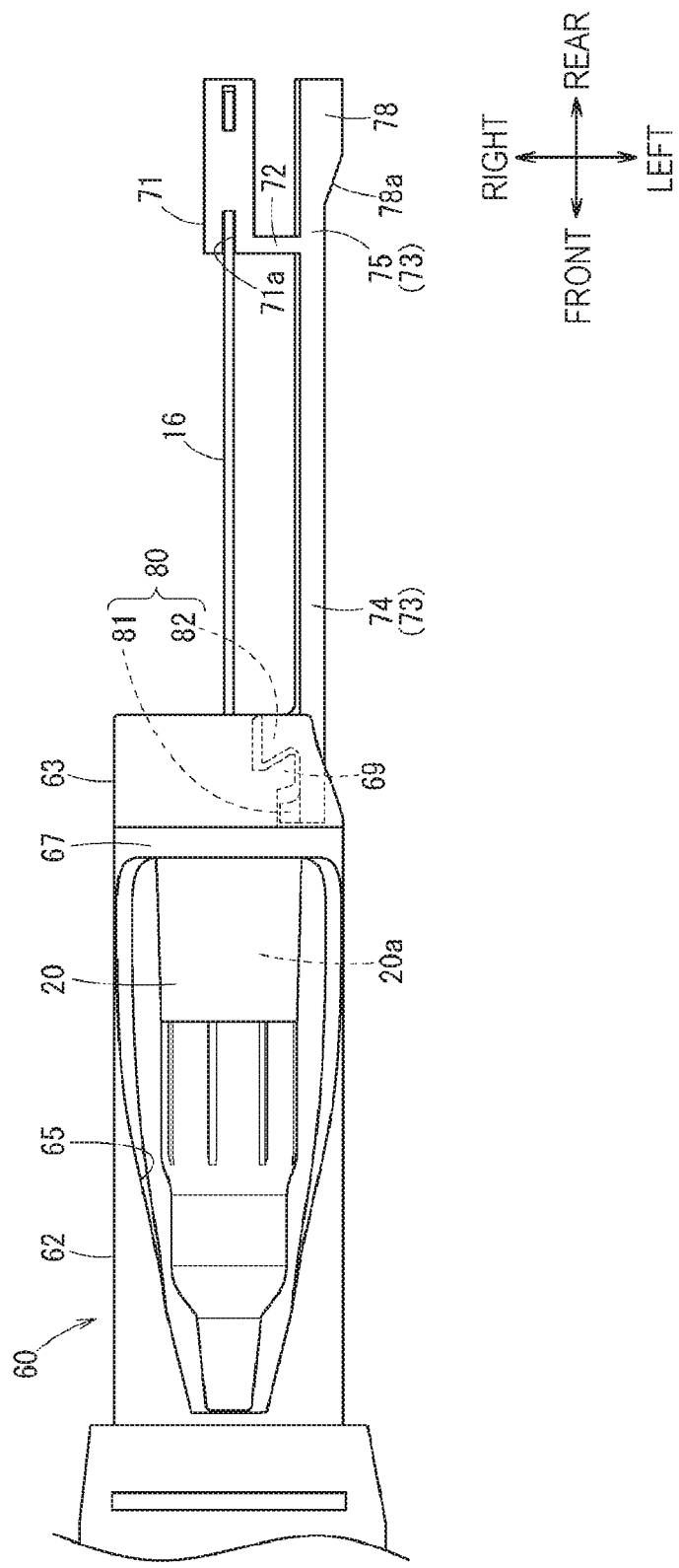

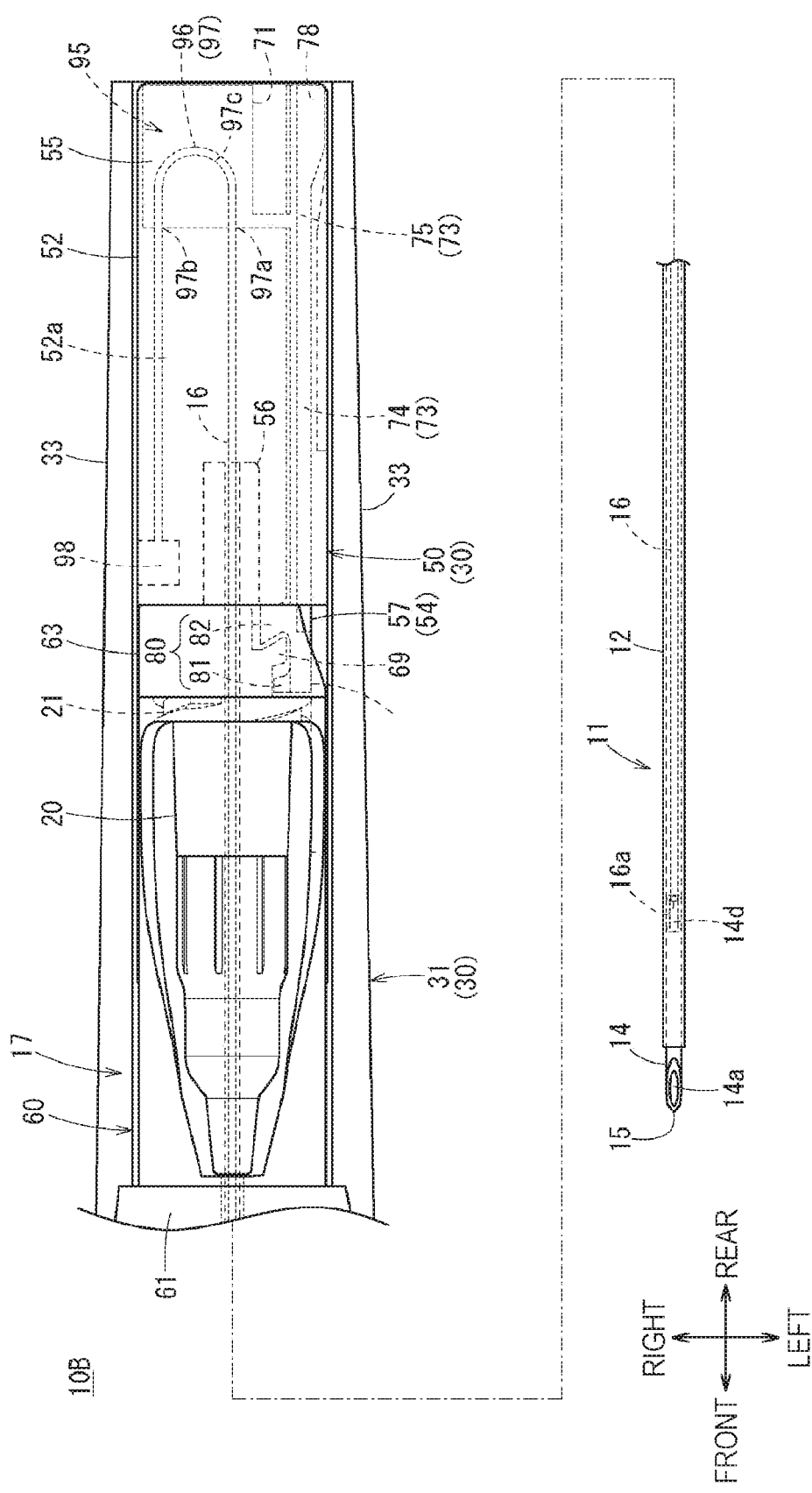

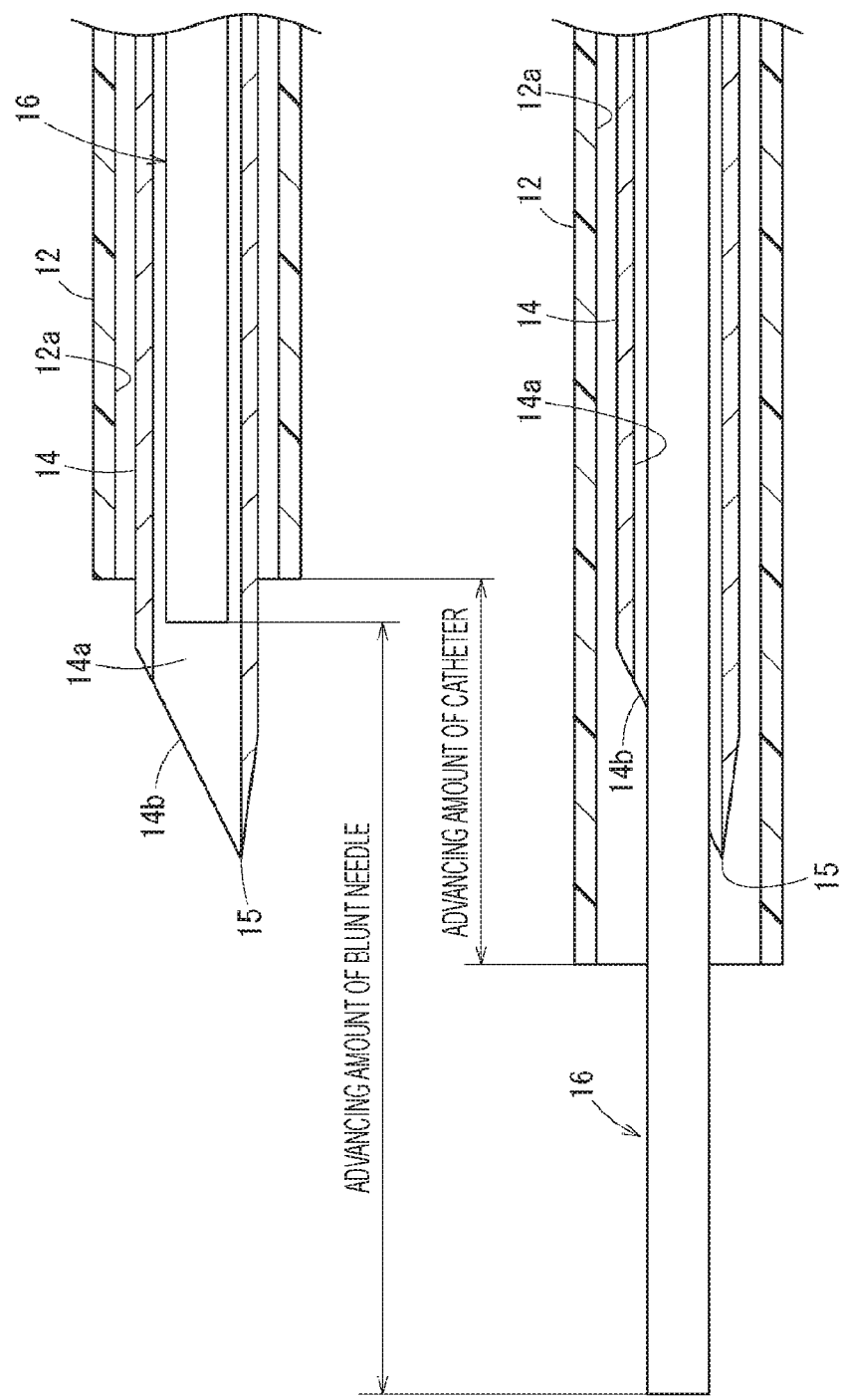

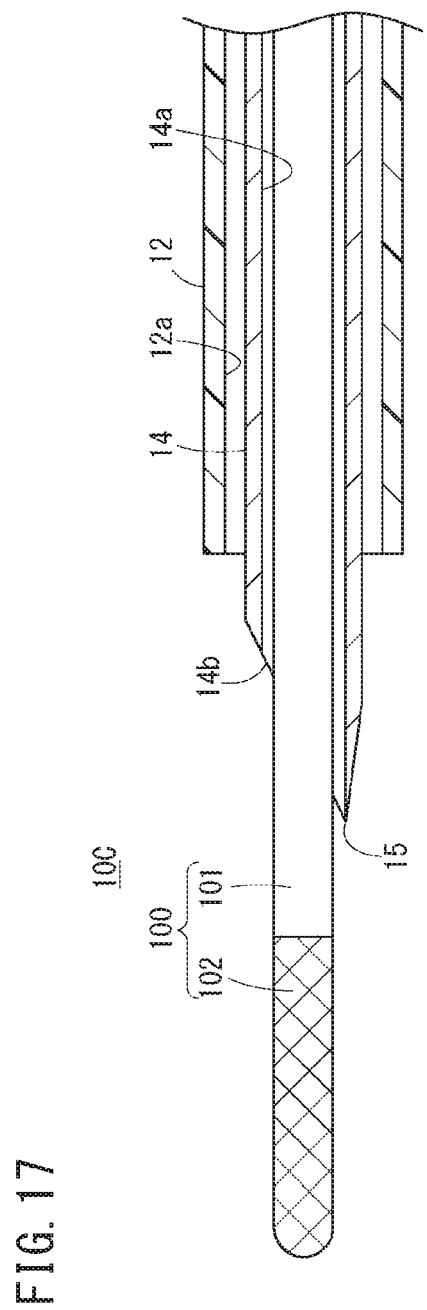

FIG. 18

| | FIRST SAMPLE | SECOND SAMPLE | THIRD SAMPLE | FOURTH SAMPLE | FIFTH SAMPLE |
|---|---|---|---|---|---|
| INNER DIAMETER OF INNER NEEDLE (mm) | 0.395 | 0.395 | 0.595 | 0.442 | 0.598 |
| OUTER DIAMETER OF BLUNT NEEDLE (mm) | 0.377 | 0.376 | 0.237 | 0.357 | 0.453 |
| LENGTH OF BACK-CUT (mm) | 0.035 | 0.105 | LANCET | 0.107 | LANCET |
| HEIGHT OF BACK-CUT (mm) | 0.029 | 0.087 | LANCET | 0.083 | LANCET |
| FIRST EXPERIMENT: PRESSING STRENGTH (N/mm) | 4.8 | 4.8 | 1.2 | 0.7 | 3.4 |
| SECOND EXPERIMENT: WEIGHT (g) OF WEIGHT | 40.77 | 84.42 | 13.17 | 10.38 | 17.50 |

CATHETER ASSEMBLY

CROSS REFERENCE TO RELATED APPLICATIONS

The present application is a continuation of and claims benefit to PCT Application No. PCT/JP2018/012177, filed on Mar. 26, 2018, entitled "CATHETER ASSEMBLY" which claims priority to Japanese Patent Application No. 2017-060706, filed Mar. 27, 2017. The entire disclosures of the applications listed above are hereby incorporated herein by reference, in their entirety, for all that they teach and for all purposes.

FIELD

The present disclosure is generally directed to a catheter assembly having an inner needle and an outer needle.

BACKGROUND

A catheter assembly, as disclosed in Japanese Patent Application JP 2015-47493 or the like, may be used to build an introducer of an infusion line for infusion on a patient. The catheter assembly disclosed in Japanese Patent Application JP 2015-47493 has a double tube needle (multitube portion) in which an inner needle is inserted into a catheter (outer needle). Use of this catheter assembly requires the user to puncture the body of the patient with the multitube portion, advance the catheter into the blood vessel, and then withdraw the inner needle from the catheter to indwell the catheter.

SUMMARY

When inserting the catheter, described in Japanese Patent Application JP 2015-47493, into the blood vessel of the patient, there is a risk that the catheter may be pierced from the inside by the inner needle when advancing the inner needle relative to the catheter (hereinafter referred to as outer needle pricking). Further, the inner needle of this catheter assembly is discarded after use in the catheter assembly, causing the risk that the exposed inner needle may prick the patient, the user, or a third person by mistake (hereinafter referred to as mispricking).

The present disclosure solves these problems and provides a catheter assembly capable of enhancing its handleability by reliably preventing outer needle pricking and/or mispricking.

In some embodiments, a catheter assembly is provided that includes a catheter, a catheter hub fixedly holding the catheter, an inner needle having a needle tip and releasably inserted into the catheter, an inner needle hub fixedly holding the inner needle, a rod member disposed in a hollow portion axially extending in the inner needle and having a distal end portion blunter than the needle tip, and a movement mechanism for moving the rod member, in which the movement mechanism is formed separately from the catheter hub, and causes the distal end of the rod member to protrude beyond the needle tip along with the movement of the catheter.

It is an aspect of the present disclosure that the catheter assembly includes the rod member and the movement mechanism, such that when the user operates the movement mechanism to advance the catheter into the blood vessel, the movement mechanism can protrude the distal end of the rod member beyond the needle tip. The rod member protruding from the needle tip can reliably prevent the outer needle pricking and the mispricking. In particular, the movement mechanism provides excellent handleability, as the movement mechanism moves the rod member along with the movement of the catheter without separately requiring the user to perform the protruding operation. Further, the catheter hub and the movement mechanism are separate bodies, such that the catheter hub may be configured such that the catheter and the catheter hub are rotated relative to the inner needle, thus further preventing the potential damage or the like to the catheter hub. This arrangement greatly increases the handleability of the catheter assembly described herein.

In some embodiments, the movement mechanism includes a rod member hub for applying a moving force to the rod member, and an engagement member for engaging the catheter hub and the rod member hub.

The movement mechanism may include the rod member hub and the engagement member, such that, as the engagement member engaged with the catheter hub is moved, the rod member hub engaged with the engagement member is moved to provide the movement force easily to the rod member.

In some embodiments, in addition to the above configuration, the engagement member may be an operation member, which can be detachably attached to the catheter hub, may be able to operate movement of the catheter hub, and moves the rod member along with the movement of the catheter hub.

In one embodiment, the user can operate the operation member to move the catheter and, by following this movement, can move the catheter hub and easily move the rod member.

The rod member hub may be movable relative to the inner needle and may comprise an engaging portion at a predetermined position, the operation member may comprise a portion to be engaged, which is engaged with the engaging portion, the engaging portion and the portion to be engaged are maintained in engagement in a pre-puncture state of the catheter and the inner needle, and released from the engagement at a position where the rod member protrudes beyond the needle tip.

The catheter assembly can move the operation member and the rod member hub together by engaging the engaging portion and the portion to be engaged. Further, the engagement is released at a position where the rod member protrudes beyond the needle tip, such that the catheter and the catheter hub can be easily moved and left indwelling on the patient side after the disengagement.

Further, the inner needle hub includes a retraction limiting portion which limits retraction of the rod member relative to the inner needle by hooking the rod member hub at a position where the engagement of the engaging portion is released.

The catheter assembly described herein can limit the retraction of the rod member hub at the position where the engaging portion is disengaged by the retraction limiting portion, such that the retraction of the rod member protruding from the needle tip can be prevented easily and reliably.

In some embodiments, the rod member hub receives an increasing moving force of the rod member hub in a direction in which the engagement of the engaging portion and the portion to be engaged is released along with the relative advancement of the rod member hub relative to the inner needle.

As the rod member hub is advanced, the moving force to move the rod member hub increases in the direction of releasing the engagement between the engaging portion and the portion to be engaged, such that the release of the engagement and limiting the retraction between the engaging portion and the portion to be engaged can be carried out smoothly at a desired position.

The inner needle hub may include a guide portion that increases the moving force to move the rod member hub along with the advancement of the rod member hub.

The guide portion can easily increase the operating force in the direction in which the engagement between the engaging portion and the portion to be engaged is released as the rod member hub advances.

The rod member hub includes a holding portion for holding the rod member, a hinge portion continuous with the holding portion and projecting in a direction perpendicular to the extending direction of the holding portion, and an arm portion continuous with the hinge portion, having the engaging portion at the distal end side, and extending in parallel with the holding portion in the pre-puncture state, in which the arm portion includes a protrusion on the proximal end side, the protrusion increasing a moving force to move the rod member hub inward from the inner needle hub when guided by the guide portion along with the advancement of the rod member hub, and the engaging portion moves in a lateral direction of the inner needle hub by the moving force to move the rod member.

The rod member hub can operate the arm portion with the hinge portion as a base point by providing the holding unit, the hinge portion, and the arm portion. The arm portion is easily guided in the guide portion of the inner needle hub to increase the moving force to move the rod member hub, such that the engaging portion can be easily deformed in the lateral direction in which the engagement is released.

The portion to be engaged may have a projection to be engaged projecting in a direction perpendicular to the moving direction of the operation member, the engaging portion may include, in the pre-puncture state, a first engaging projection located on the distal end side of the projection to be engaged and capable of engaging the projection to be engaged and a second engaging projection located on a proximal end side of the projection to be engaged and capable of engaging the projection to be engaged, and the second engaging projection may project beyond the first engaging projection and, in a state where the engagement of the first engaging projection and the projection to be engaged is released, the projection to be engaged and the second engaging projection overlap in a front view of the catheter assembly.

In the catheter assembly, when the rod member is not protruded, the first engaging projection is engaged with the projection to be engaged when the operation member is advanced, such that the rod member hub can smoothly follow and advance. Further, the projection to be engaged is engaged with the second engaging projection when the operation member is retracted, such that the rod member hub can be smoothly followed and retracted. Then, even when the first engaging projection and the projection to be engaged are disengaged from each other, the second engaging projection and the projection to be engaged overlap in a front view of the catheter assembly, such that, when the operation member is retracted, it is possible to engage again and follow and retract the rod member hub accordingly.

The rod member hub may include at least one folded portion that is slidably inserted into the rod member that extends in the proximal direction from the inner needle and folded back in the distal direction.

The catheter assembly includes the folded portion for folding back the rod member, such that, when the rod member hub (folded portion) is advanced, the rod member can advance by combining the portion of the rod member extending in the proximal direction and the portion extending in the distal direction. That is, the advancing amount of the rod member can be increased twice or more than the advancing amount of the rod member hub, when the folded portion of the rod member hub advances, and the rod member can be delivered earlier from the needle tip of the inner needle.

The distal end of the rod member may be located on the proximal end side of a hole communicating the outside of the inner needle with the hollow portion in the pre-puncture state of the catheter and the inner needle.

The catheter assembly can evacuate the blood flowing through the hollow portion of the inner needle, when the inner needle has punctured the patient, as the distal end of the rod member is disposed on the proximal end side of the hole of the inner needle. This allows the user to view the blood flashback well.

The distal end of the rod member is located on the distal end side of the hole communicating the outside of the inner needle with the hollow portion in the pre-puncture state of the catheter and the inner needle, and the rod member includes a flowing channel in a range from the at least distal end to the hole.

The catheter assembly can evacuate the blood flowing through the hollow portion of the inner needle through the flowing channel from the hole, when the inner needle has punctured the patient, as the distal end of the rod member is disposed on the distal end side of the hole of the inner needle.

In some embodiments, the rod member includes, when in a protruding state from the inner needle, a hard portion on the proximal end side of the protrusion and a soft portion on the distal end side of the protrusion, the soft portion being softer than the hard portion.

The rod member has the soft portion at the distal end of the hard portion, whereby the rod member can be used flexibly without trouble even when the rod member touches the catheter, the patient, the user, or the third person and can favorably prevent the outer needle pricking or mispricking.

The inner needle may include a blade surface, and the rod member may prevent the catheter from piercing the rod member by the inner needle, when the rod member and the catheter are made to protrude beyond an end of the inner needle and the catheter is advanced and retracted, with a weight of 30 grams being attached to distal end of the catheter, the needle tip being arranged horizontal, and a blade surface of the inner needle facing vertically downward.

Thus, the rod member can prevent the inner needle from piercing the catheter. For instance, the rod member protruding from the inner needle provides a portion of material at the sharpened end of the inner needle that, among other things, can resist bending of the catheter relative to the inner needle. Without this protruding rod member, the catheter could be bent relative to the inner needle at the sharpened end allowing the inner needle to pierce the catheter.

According to the embodiments of the present disclosure, the catheter assembly reliably prevents outer needle pricking and/or mispricking and enhances the safe handling and operation of the catheter assembly.

BRIEF DESCRIPTION OF THE DRAWINGS

FIG. 6 is a plan view illustrating a state in which the catheter operation member and a blunt needle hub of FIG. 1 are assembled in accordance with embodiments of the present disclosure;

FIG. 15 is a plan view illustrating the catheter assembly in a pre-puncture state according to a third embodiment of the present disclosure;

FIG. 16 is a side sectional view illustrating the operation of the blunt needle of the catheter assembly of FIG. 15 in accordance with embodiments of the present disclosure;

FIG. 17 is a side sectional view illustrating a catheter assembly according to a fourth embodiment of the present disclosure;

FIG. 18 is a table illustrating experimental results of first to fifth samples including the catheter assembly in accordance with embodiments of the present disclosure;

DETAILED DESCRIPTION

Hereinafter, embodiments of the catheter assembly according to the present disclosure will be described in detail with reference to the accompanying drawings.

First Embodiment

Figure 1:
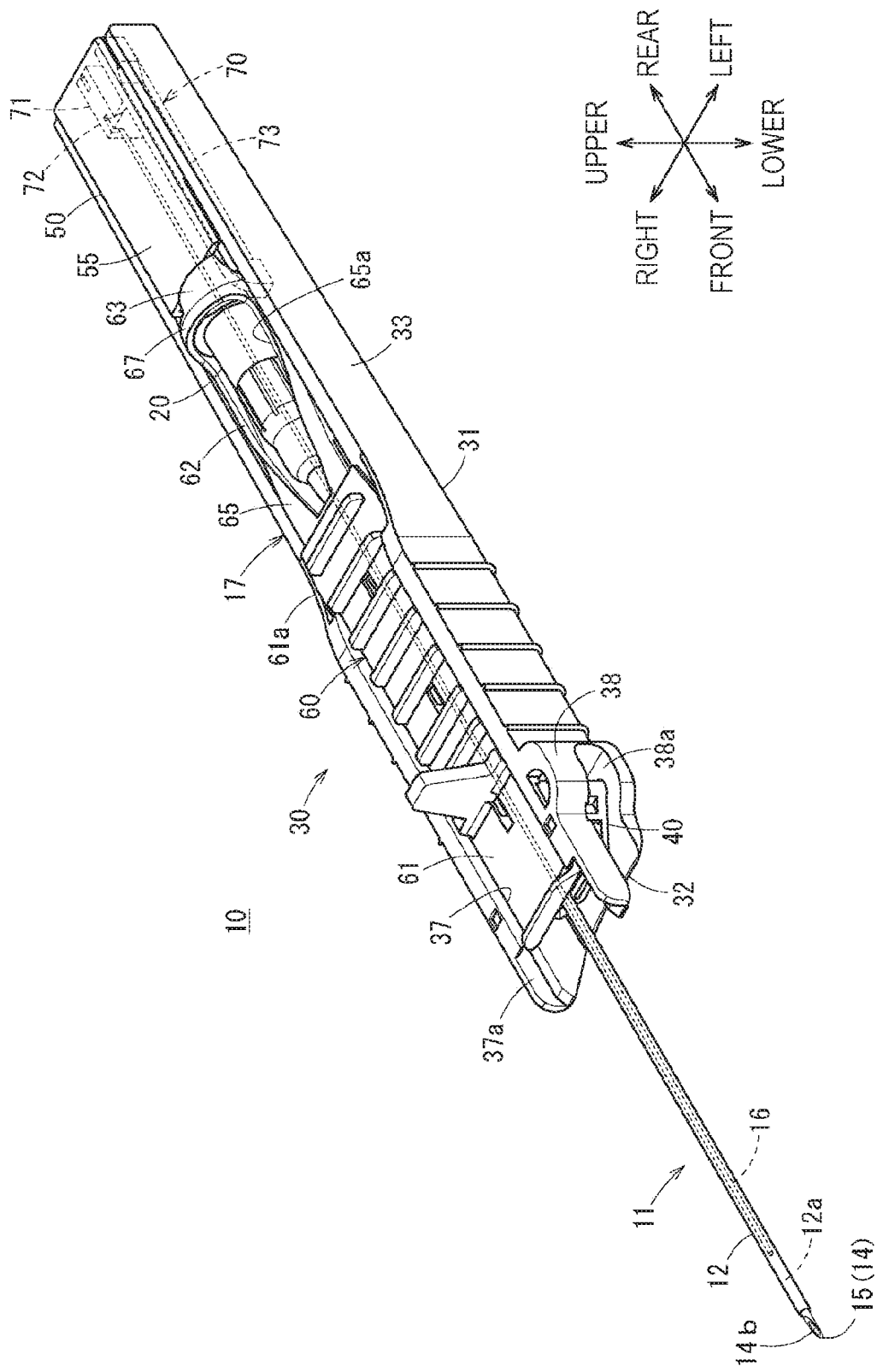
FIG. 1 is a perspective view of a catheter assembly according to a first embodiment of the present disclosure.

FIG. 1 is a perspective view of a catheter assembly 10 according to a first embodiment of the present disclosure. A catheter assembly 10, as described herein, may be used when performing infusion, transfusion, and the like on a patient (e.g., a living body, etc.), and may correspond to a medical device for building an introducer of, for example, a drug solution by puncturing the body of the patient with a catheter 12 and indwelling the catheter 12 in the body of the patient. The catheter assembly 10 may be configured to allow insertion of a catheter (e.g., a central vein catheter, a PICC, a midline catheter, etc.) which may be longer than a catheter for peripheral veins. Alternatively, the catheter assembly 10 may be configured to allow insertion of a peripheral vein catheter. The catheter assembly 10 is not limited to be used to insert a venous catheter, but may also be used to insert an arterial catheter such as a peripheral arterial catheter, etc.

As illustrated in FIG. 1, the catheter assembly 10 includes a catheter 12, a catheter hub 20, an inner needle 14, an inner needle hub 30, and a catheter operation member 60. In addition, the catheter assembly 10 may comprise a blunt needle 16 and a blunt needle hub 70 for supporting the blunt needle 16 as a safety function to prevent the outer needle pricking and/or the misprick described above. In use, the blunt needle 16 may be projected from the inner needle 14 some distance past the sharpened end thereof. As used in the present embodiment, the "blunt needle" 16 is the name used for convenience of explanation, and may refer to a rod member configured not to puncture the living body.

The catheter assembly 10 includes a multitube portion 11 in which the inner needle 14, the catheter 12, and the blunt needle 16 overlap in before use (in a pre-puncture state). In the multitube portion 11, a needle tip 15 of the inner needle 14 protrudes beyond a distal end of the catheter 12, and the blunt needle 16 is located on the proximal end side of the needle tip 15 (in the inner needle 14). The inner needle hub 30 constitutes a grip portion on the proximal end side of the catheter assembly 10. The inner needle hub 30 stores, in addition to the proximal end portion of the multitube portion 11, the catheter hub 20, the catheter operation member 60, and the blunt needle hub 70.

Figure 2A:
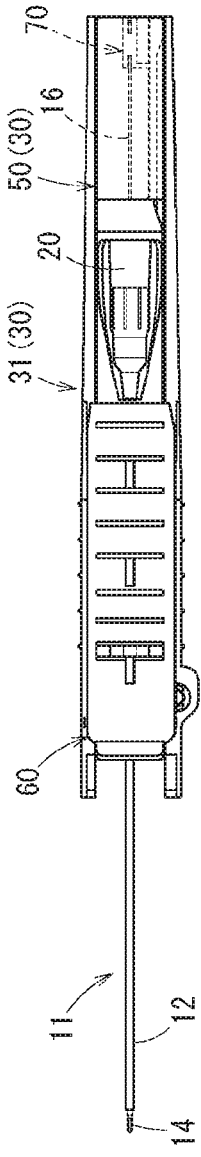
FIG. 2A is a first plan view illustrating a first operation of the catheter assembly of FIG. 1 in accordance with embodiments of the present disclosure.

First, in order to facilitate the understanding of the catheter assembly 10, the operation of the catheter assembly 10 in use will be described. In use of the catheter assembly 10, a user, such as a physician or nurse, grasps the inner needle hub 30 and punctures the patient's blood vessel (e.g., vein or artery, etc.) with the distal end of the inner needle 14 and catheter 12. While maintaining the catheter assembly 10 in the punctured state, the user advances the catheter operation member 60 in the distal direction relative to the inner needle hub 30 as illustrated in FIG. 2A to advance the catheter 12 and the catheter hub 20. When the catheter operation member 60 is initially advanced, the blunt needle 16 and the blunt needle hub 70 are also moved together with the movement of the catheter operation member 60.

Figure 2B:
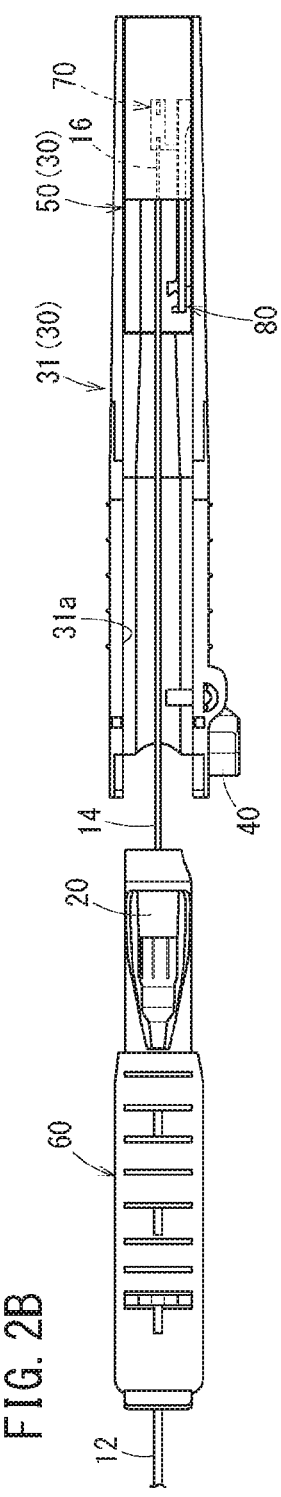
FIG. 2B is a second plan view illustrating a second operation of the catheter assembly following the first operation shown in FIG. 2A.

When the catheter operation member 60 is advanced for a predetermined length, the blunt needle hub 70 is detached from the catheter operation member 60 at a predetermined position. At this time, the distal end of the blunt needle 16 projects beyond the needle tip 15 of the inner needle 14 (see, e.g., FIG. 2C), and enters a state in which the movement is stopped in both the distal direction and the proximal direction. Therefore, the outer needle pricking, in which the inner needle 14 pricks the moving catheter 12, is prevented. As illustrated in FIG. 2B, the catheter operation member 60 causes the catheter 12 and the catheter hub 20 to advance when the blunt needle hub 70 is advanced after the detachment. At the time of late advancement (or also at the initial advancement), an operation of relatively retracting the inner needle hub 30 with respect to the catheter operation member 60 may be performed.

Figure 2C:
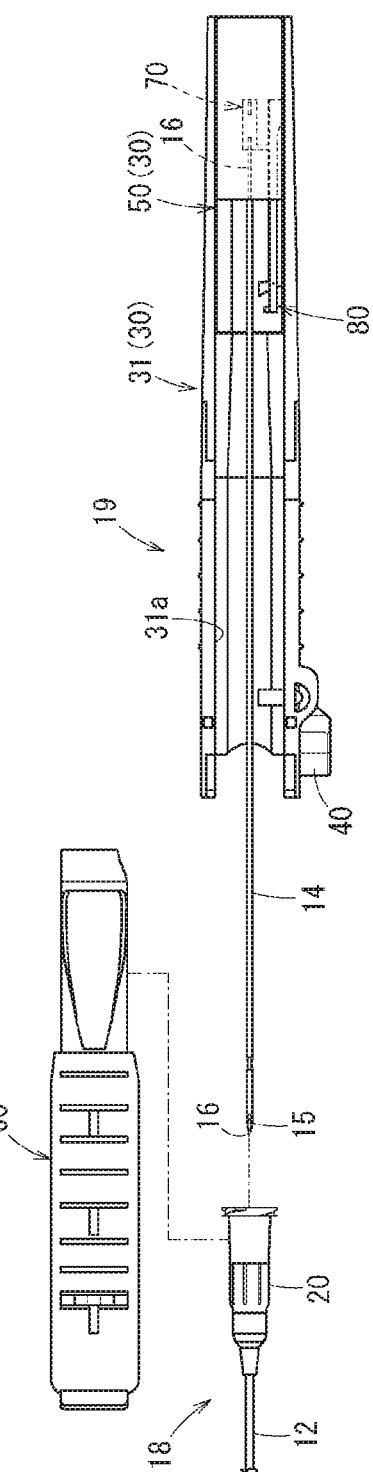
FIG. 2C is a third plan view illustrating a third operation of the catheter assembly following the second operation shown in FIG. 2B.

As illustrated in FIG. 2C, the catheter 12, the catheter hub 20, and the catheter operation member 60 advance beyond the tip of the blunt needle 16, and the catheter operation member 60 is detached, whereby the catheter assembly 10 is separated into an indwelling assembly 18 and a waste assembly 19. The indwelling assembly 18 is a catheter 12 and a catheter hub 20 and may be indwelled on the patient side. The waste assembly 19 may include the inner needle 14, the inner needle hub 30, the blunt needle 16 and the blunt needle hub 70, and can be appropriately discarded by the user.

The waste assembly 19 projects the distal end of the blunt needle 16 from the needle tip 15 of the inner needle 14 so that the needle tip 15 can be prevented from pricking the user or a third person. In some embodiments, the blunt needle 16 may be locked in the protruded position relative to the inner needle (e.g., via the interaction between the blunt needle hub 70 and the retraction limiting mechanism 77, etc.). Among other things, this "locking" prevents an unintentional retraction of the blunt needle 16 into the inner needle 14. As can be appreciated, an unintentional retraction could expose the sharp needle tip 15 of the inner needle 14 increasing the risk of mispricking a user. Hereinafter, the structures with which the catheter assembly 10 is operated will be described in accordance with embodiments of the present disclosure.

Figure 3:
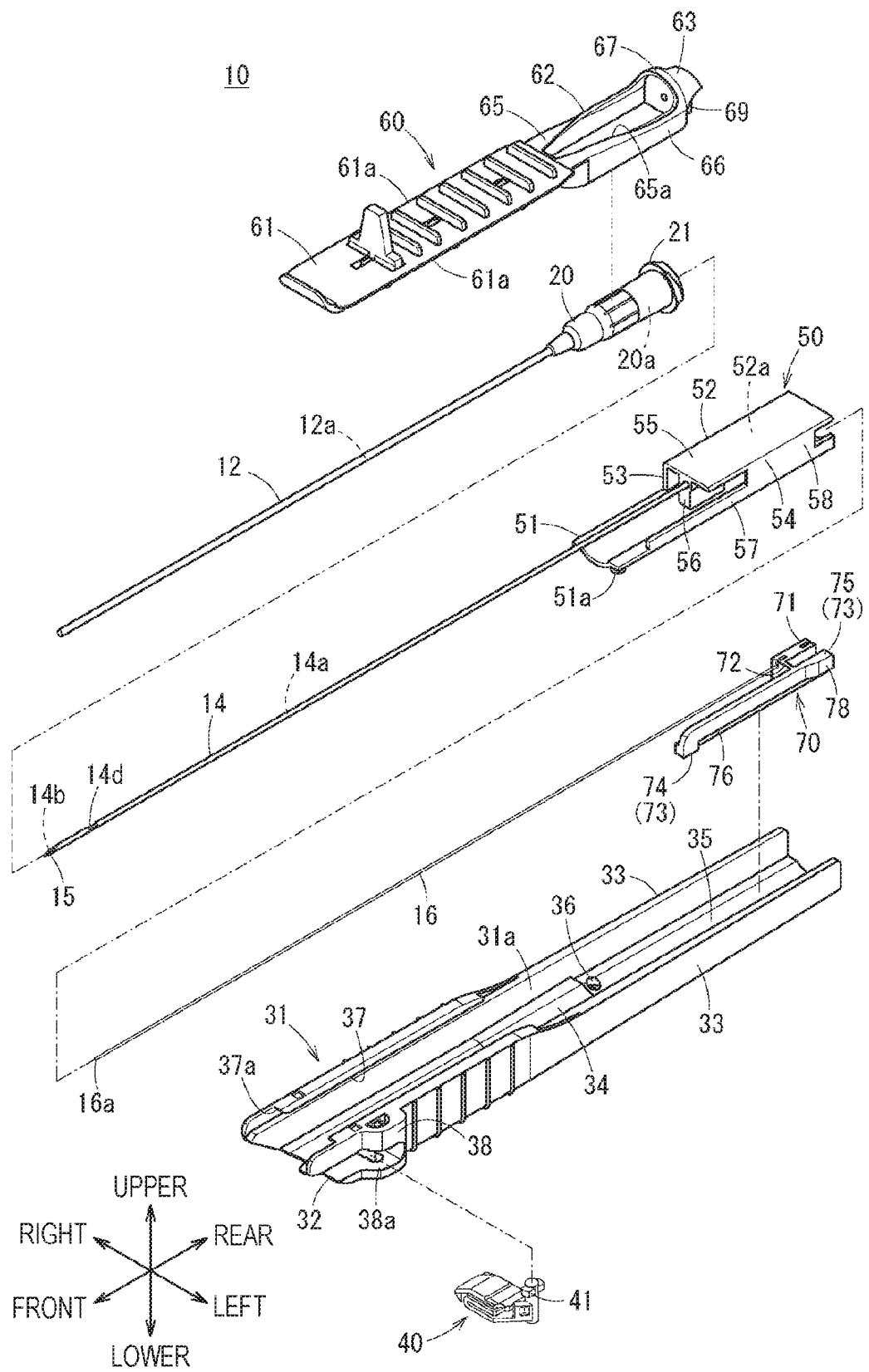
FIG. 3 is an exploded perspective view of the catheter assembly of FIG. 1 in accordance with embodiments of the present disclosure.

As illustrated in FIGS. 1 and 3, the catheter 12 of the catheter assembly 10 includes a lumen 12a having an appropriate flexibility and axially penetrating through the catheter 12. The lumen 12a is formed to have a diameter capable of accommodating the inner needle 14 and capable of flowing a drug solution, blood, and/or the like. The length of the catheter 12 is not particularly limited and can be appropriately designed according to any application, conditions, and so on. For example, the length of the catheter 12 may be set to about 14 mm to 500 mm, 30 mm to 400 mm, or 76 mm to 200 mm.

A constituent material of the catheter 12 is not particularly limited, and may be a soft resin material such as, for example, fluorine resins such as polytetrafluoroethylene (PTFE), ethylene/tetrafluoroethylene copolymer (ETFE), perfluoroalkoxy fluorine resin (PFA), or the like, olefin resins such as polyethylene and polypropylene, or mixtures thereof, polyurethane, polyester, polyamide, polyether nylon resin, mixtures of olefin resin and ethylene/vinyl acetate copolymer, or the like.

The proximal end portion of the catheter 12 is secured to the distal end portion within the catheter hub 20 by an appropriate securing means such as caulking, fusion, adhesion, or the like. The catheter hub 20 is exposed on the skin of the patient with the catheter 12 inserted into the blood vessel of the patient, affixed with a tape or the like, and indwelled together with the catheter 12.

The catheter hub 20 is formed in a tubular shape tapered in the distal direction. At the proximal end of the outer peripheral surface of the catheter hub 20, a flange portion 21 projecting radially outward is provided. Inside the catheter hub 20, an internal space 20a is provided which is in fluid communication with the lumen 12a of the catheter 12 and through which an infusion can flow. The internal space 20a accommodates a hemostatic valve (not illustrated) for preventing backflow of blood when making a puncture with the inner needle 14, and a plug (not illustrated) which allows infusion through the hemostatic valve when the connector of the infusion tube is inserted or the like.

The constituent material of the catheter hub 20 is not particularly limited, and may be made of, for example, thermoplastic resins such as polypropylene, polycarbonate, polyamide, polysulfone, polyarylate, methacrylate-butylene-styrene copolymer, or the like.

The inner needle 14 of the catheter assembly 10 is configured as a hollow tube having a rigidity capable of piercing the skin of a living body. A sharp needle tip 15 is formed at the distal end of the inner needle 14. The needle tip 15 is formed in a back-cut shape in which the opposite side of the blade surface is cut in a tapered shape (see also FIG. 14A and the like). The shape of the needle tip 15 is not particularly limited, and may be formed, for example, by simply cutting the blade surface obliquely with respect to the axial center of the inner needle 14 or formed in a lancet shape by forming a peak in a widthwise center of two right and left blade surfaces. A hollow portion 14a is provided in the inner needle 14 in the axial direction, and the hollow portion 14a has a distal end opening 14b provided at the needle tip 15 and a proximal end opening 14c (see, e.g., FIG. 4A) provided at the proximal end of the inner needle 14. In some embodiments, a hole 14d communicating the hollow portion 14a with the outside of the inner needle 14 is provided at a position slightly offset from the needle tip 15 in the proximal direction.

Examples of the constituent material of the inner needle 14 may include, but are in no way limited to, stainless steel, a metal material such as aluminum or an aluminum alloy or titanium or a titanium alloy, hard resin, ceramics, and/or the like. The inner needle 14 may be firmly fixed to the inner needle hub 30 by an appropriate fixing means such as fusion, adhesion, or insert molding.

The inner needle hub 30 is a structural portion fixedly holding the inner needle 14 and moving together with the inner needle 14 and, in the present embodiment, provided as a grip portion to be gripped by the user formed by assembling a plurality of members. The plurality of members may include a housing 31, a support member 40, and a needle holding member 50.

The housing 31 includes a lower wall 32 and a pair of side walls 33 projecting upward from both sides of the lower wall 32, and a housing space 31a is formed in the housing 31. In one embodiment, the housing 31 may be formed as a substantially U-shaped channel providing the housing space 31a between the pair of side walls 33 and the lower wall 32. The resin material forming the housing 31 is not specifically limited and may be selected appropriately from, for example, the materials mentioned in connection with the catheter hub 20.

The lower wall 32 has a guide groove 34 in which a widthwise central portion is recessed downward. The proximal end side from the middle portion of the lower wall 32 in the longitudinal direction is formed thinner than the distal end side in the longitudinal direction to form an arrangement portion 35 to which the needle holding member 50, described later, is attached and/or formed. Further, a plurality of (e.g., two or more, etc.) mounting holes 36 for mounting the needle holding member 50 may be provided at appropriate places of the lower wall 32.

The pair of side walls 33 extends in parallel with the lower wall 32 in the longitudinal direction, and grooved rail portions 37 are provided on the inner surface of the distal end side which is formed higher than the proximal end side. The pair of rail portions 37 continues to an open portion 37a formed on the upper portion of the distal end side of the side walls 33, while continuing to the upper surface of each side wall 33 on the proximal end side. The pair of rail portions 37 slidably accommodates, and keys, side edges 61a of the catheter operation member 60. Further, the open portion 37a may be cut out toward the upper side of the housing 31 to allow bending of the catheter operation member 60. One of the pair of side walls 33 (e.g., the left side wall 33 shown in FIG. 1, etc.) has a bulging portion 38 bulging outward in the width direction. The bulging portion 38 has an attaching recess 38a for attaching the support member 40.

The support member 40 is attached to support the lower side of the catheter 12 (multitube portion 11) held by the catheter operation member 60. The support member 40 is rotatably mounted in the attaching recess 38a to support the catheter 12 with an appropriate elasticity in a pre-puncture state. Inside the support shaft of the support member 40 in the width direction, a guide recess 41 connected to the rail portions 37 is provided. In the guide recess 41, the side edges 61a of the catheter operation member 60 are disposed in a pre-puncture state.

With the side edges 61a of the catheter operation member 60 being present in the guide recess 41 when the catheter operation member 60 is stored in the housing 31, the support member 40 can support the catheter 12 by limiting the rotation of the support member 40 and keeping the catheter 12 in a waiting mode. Thus, the catheter 12 is supported from below, so that the deflection of the catheter 12 is prevented. When the catheter operation member 60 comes out of the housing 31, the support member 40 becomes rotatable as the side edges 61a come out of the guide recess 41. Further, the support member 40 can further rotate outward of the side walls 33 when the catheter operation member 60 comes into contact with the support member 40, as illustrated in FIG. 2B. Accordingly, the catheter hub 20 and the catheter operation member 60 may be smoothly delivered from the housing 31.

The needle holding member 50 attached to the housing 31 is a member to which the inner needle 14 is directly fixed, and is accommodated and fixed inside the housing 31. Further, the needle holding member 50 constitutes a part of a movement mechanism 17 for moving the blunt needle 16, such that the needle holding member 50 has a guiding function to guide the movement of the blunt needle hub 70, while limiting advancement and retraction of the blunt needle hub 70 at a predetermined position.

Figure 4A:
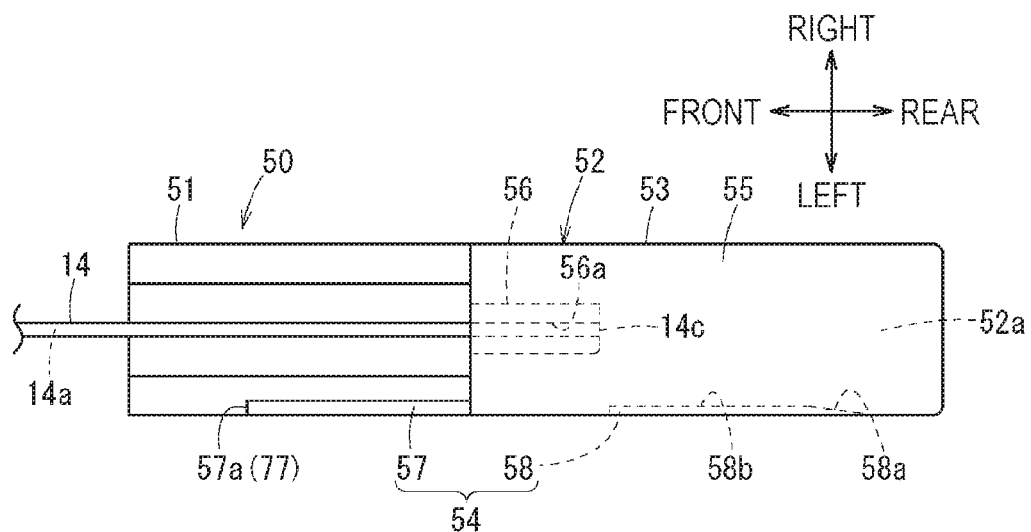
FIG. 4A is a plan view illustrating a needle holding member of the catheter assembly of FIG. 1 in accordance with embodiments of the present disclosure.
Figure 4B:
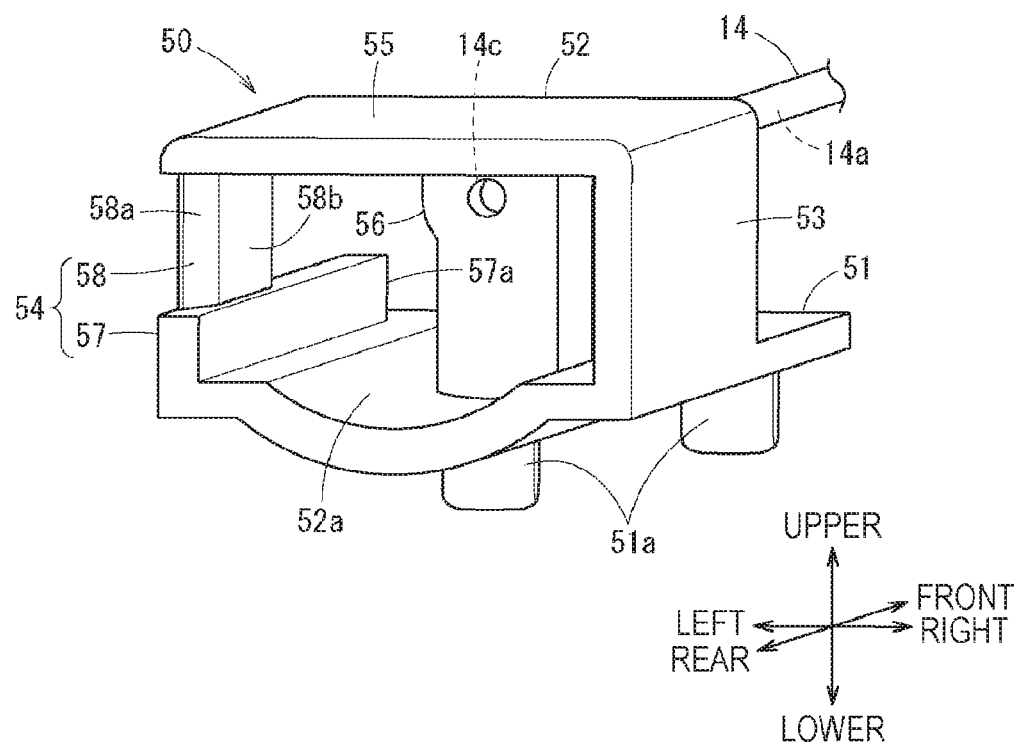
FIG. 4B is a perspective view of the needle holding member of FIG. 4A as viewed from a proximal end side thereof in accordance with embodiments of the present disclosure.

As illustrated in FIGS. 3, 4A, and 4B, the needle holding member 50 may be formed to have a width to be inserted into the housing space 31a of the housing 31 and includes a mounting plate 51 mounted to the lower wall 32. The mounting plate 51 has a circular-arc shaped cross-section with its widthwise central portion being recessed downward so as to fit the arrangement portion 35 (guide groove 34) of the lower wall 32. The lower surface of the mounting plate 51 is provided with a plurality of mounting protrusions 51a, which are respectively inserted and fixed to the plurality of mounting holes 36.

Further, the needle holding member 50 includes a frame structure 52 to form the needle holding member 50 substantially in the shape of a rectangular tube from the middle portion to the proximal end side of the mounting plate 51. The frame structure 52 has a side frame 53 on one side of the mounting plate 51 in the width direction (e.g., in the upper side shown in FIG. 4A), a guide frame 54 on the other side of the mounting plate 51 in the width direction (e.g., in the lower side shown in FIG. 4A), and a cover portion 55 for bridging the upper portions of the side frame 53 and the guide frame 54. Inside the mounting plate 51 and the frame structure 52 (e.g., including the side frame 53, the guide frame 54, and the cover portion 55), an attaching space 52a in which the blunt needle hub 70 is slidably disposed is formed.

In some embodiments, in the vicinity of the distal end portion of the cover portion 55, a holding body 56 for holding the inner needle 14 may be continuously provided between the cover portion 55 and the mounting plate 51. The holding body 56 may be formed in a block shape with its proximal end surface defining a movement limit of the blunt needle hub 70 in the distal direction. Further, a holding hole 56a may be provided for holding the inner needle 14 at a predetermined height position of the holding body 56. The holding hole 56a penetrates through the inside of the holding body 56 in a front-rear direction (axial direction of the housing 31) to connect and fix the proximal end portion of the inner needle 14 in the axial direction.

The guide frame 54 of the frame structure 52 can be divided into a lower guide portion 57 and an upper guide portion 58. The lower guide portion 57 protrudes low from the upper surface of the mounting plate 51 and extends from the proximal end of the needle holding member 50 beyond the cover portion 55 in the distal direction. The distal end of the lower guide portion 57 may be located on a slightly proximal end side beyond the distal end of the mounting plate 51. This distal end may be formed on a flat surface orthogonal to the extending direction of the needle holding member 50 to provide a retraction limiting surface 57a (retraction limiting portion) which limits the retraction of the blunt needle hub 70.

The upper guide portion 58 is provided continuously from the upper portion of the lower guide portion 57 to the cover portion 55. The dimension of the upper guide portion 58 in the height direction is longer than the dimension of the lower guide portion 57 in the height direction. Meanwhile, the upper guide portion 58 extends in the same direction as the lower guide portion 57 with a dimension shorter than the extension length of the cover portion 55. On the proximal end side of the upper guide portion 58, an inclined surface 58a is formed to be inclined inward in the width direction inside the frame structure 52 from the most proximal end toward the distal direction. On the distal end side of the inclined surface 58a of the upper guide portion 58, a flat surface 58b parallel to the side frame 53 is provided.

Figure 5:
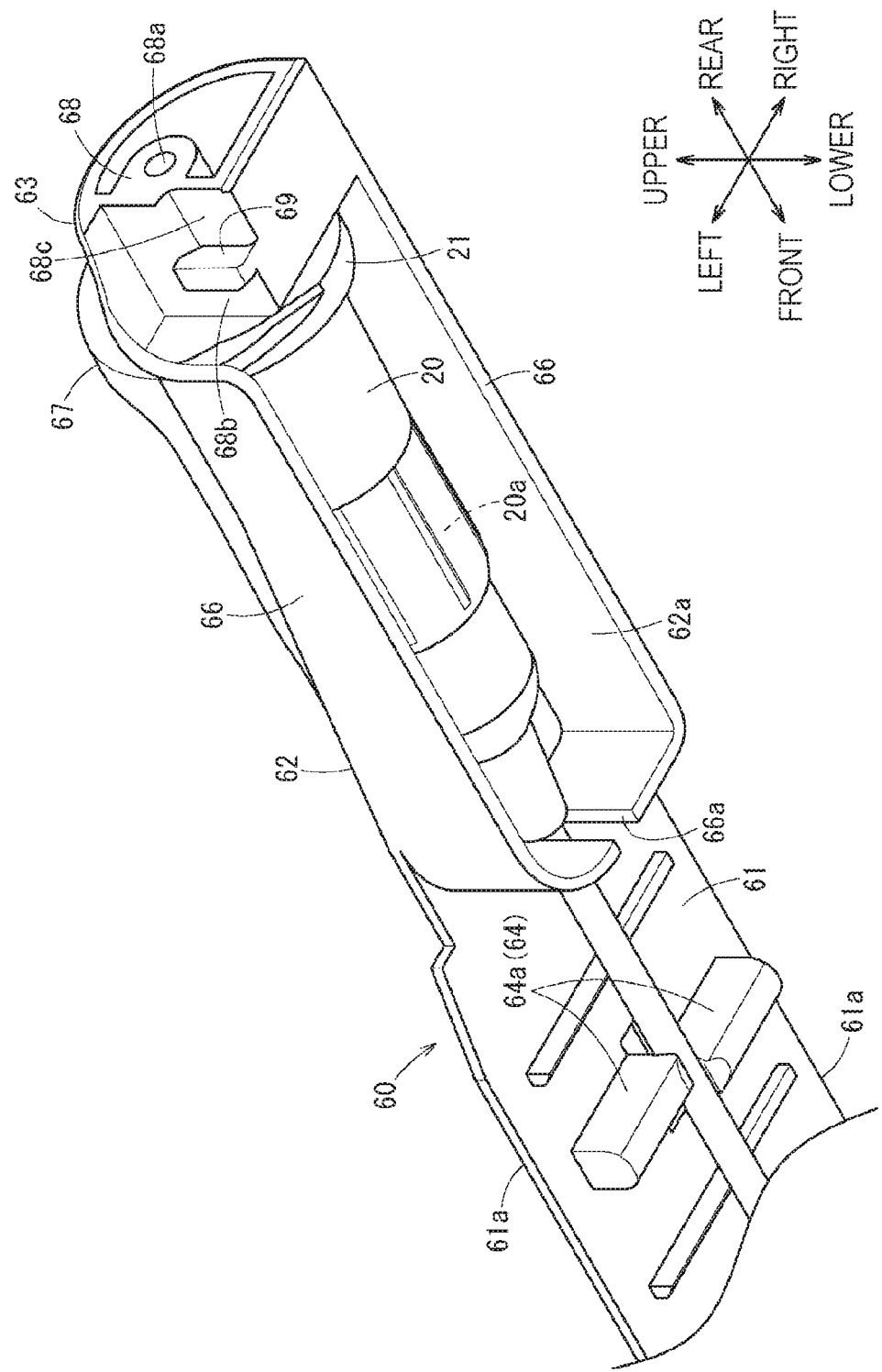
FIG. 5 is a perspective view of the catheter operation member of the catheter assembly of FIG. 1 as viewed from the proximal end side and the lower side thereof in accordance with embodiments of the present disclosure.

As illustrated in FIGS. 3 and 5, the catheter operation member 60 directly holds the catheter 12 and is attached to the catheter hub 20, so that the catheter 12 and the catheter hub 20 can be advanced and retracted (e.g., moved relatively) with respect to the inner needle 14 and the housing 31. The catheter operation member 60 includes an operation plate portion 61 extending in the longitudinal direction of the housing 31, a hub storage portion 62 connected to the proximal end of the operation plate portion 61 and accommodating the catheter hub 20, and a portion to be engaged 63 connected to the proximal end of the hub storage portion 62 and engageable with the blunt needle hub 70.

The operation plate portion 61 is a portion pressed by a finger of the user to perform advancing and retracting operations. In the pre-puncture state, the pair of side edges 61a of the operation plate portion 61 are disposed on the pair of rail portions 37 of the inner needle hub 30 (housing 31) and the upper surface of the pair of side walls 33. The operation plate portion 61 is formed to be thin so as to be flexible enough to be bent in a direction away from the inner needle 14. The material of the operation plate portion 61 (catheter operation member 60) is not specifically limited and may be selected appropriately from the materials, for example, listed in the connection with the catheter hub 20, etc.

On the lower surface of the operation plate portion 61, one or more catheter holding portions 64 are formed by pairs of projecting pieces 64a and provided along the longitudinal direction. The catheter holding portions 64 are arranged at equal intervals in the longitudinal direction of the operation plate portion 61 and grip the catheter 12 by each pair of projecting pieces 64a at each location. When the operation plate portion 61 is bent, the pairs of projecting pieces 64a sequentially release the grip of the catheter 12.

The hub storage portion 62 of the catheter operation member 60 includes an upper plate 65 connected to the operation plate portion 61 and a pair of side plates 66 projecting downward from the upper plate 65, and a storage chamber 62a is formed inside the upper plate 65 and the pair of side plates 66. The lower side of the storage chamber 62a is open.

The upper plate 65 is provided with a disposition hole 65a cut out in a substantially isosceles triangle shape in accordance with the shape of the catheter hub 20. The disposition hole 65a exposes the catheter hub 20 disposed in the storage chamber 62a. The pair of side plates 66 extend in parallel with the side walls 33 of the housing 31 and shield the storage chamber 62a with the distal end sides of the side plates 66 curved inward. Further, the distal end sides of the pair of side plates 66 form a gap 66a which is narrower than the catheter hub 20 and from which only the catheter 12 (e.g., the multitube portion 11) extends. The lower side of the gap 66a is open.

On the proximal end side of the hub storage portion 62, an arch portion 67, which bridges over the pair of side plates 66 in an arc shape is provided. The pair of side plates 66 and the arch portion 67 come into contact with the flange portion 21 of the catheter hub 20 to provide an appropriate frictional force therebetween. That is, the catheter hub 20 is separably held by a suitable frictional force from the hub storage portion 62. In the hub storage portion 62, for example, after the catheter hub 20 is removed from the housing 31, the user pushes a finger through the disposition hole 65a pushing the catheter hub 20 downward to remove the catheter hub 20 from the catheter operation member 60.

The portion to be engaged 63 of the catheter operation member 60 has a semicircular appearance according to the outer shape of the hub storage portion 62, and is formed in a partially cut-out frame shape when viewed from the proximal end side (see, e.g., FIG. 5). In a middle frame 68 located in the center of the portion to be engaged 63 in the width direction, an insertion hole 68a through which the inner needle 14 runs is formed. Further, in the cut-out portion of the portion to be engaged 63, a projection to be engaged 69 protrudes from the side surface of the middle frame 68.

As illustrated in FIGS. 5 and 6, the projection to be engaged 69 protrudes from the middle frame 68 so as to be inclined outward in the width direction and toward the proximal end side. The projection to be engaged 69 is formed in a rectangular column shape and protrudes a small distance, while having a certain thickness, thus providing a mechanism to engage the blunt needle hub 70 in the distal end and proximal end directions. Specifically, this mechanism illustrated in the present embodiment has a hooking function. In the middle frame 68, a side surface 68b located on the distal end side of the projection to be engaged 69 is located farther outside in the width direction than a side surface 68c located on the proximal end side of the projection to be engaged 69. That is, the side surfaces 68b and 68c are formed uneven across the projection to be engaged 69.

Referring to FIGS. 1 and 3 again, the blunt needle 16 and blunt needle hub 70 of the catheter assembly 10 will be described in accordance with embodiments of the disclosure. The blunt needle 16 may be formed in a round bar shape that extends longer than the inner needle 14 and is slidably inserted into the inner needle 14 and the housing 31 to configure the multitube portion 11.

The thickness of the blunt needle 16 may be appropriately designed in accordance with the thickness of the inner needle 14 and, for example, may be slightly thinner than the hollow portion 14a. The blunt needle 16 may have a desired rigidity depending on its constituent material and thickness. For example, the actual size of the outer diameter may be 0.19 mm to 1.19 mm. The outer diameter of the blunt needle 16 may be smaller than the inner diameter of the inner needle 14 by, for example, 0.01 mm to 0.20 mm. Accordingly, the shaking or the like of the blunt needle 16 is prevented when exposed from the needle tip 15, and maintains the straightness along the axial center on the proximal end side.

The distal end surface 16a of the blunt needle 16 is formed blunter than the needle tip 15 of the inner needle 14 and is, for example, formed as a flat surface (see, e.g., FIG. 13A) obtained by cutting and polishing a previous body of the rod member. In some embodiments, the distal end surface 16a, a peripheral surface, and corner portions of the blunt needle 16 may be formed in an R-shape. The blunt needle 16 is not particularly limited as long as it is configured not to easily pierce the living body or the catheter 12, and can be formed in various shapes. Other shapes include a hemispherical shape (see, e.g., FIG. 17) and/or the like. The proximal end of the blunt needle 16 is firmly fixed to the holding portion 71 of the blunt needle hub 70 by an appropriate fixing means such as welding, adhesion, and/or the like.

The material constituting the blunt needle 16 is not particularly limited as long as sufficient rigidity can be obtained, and may include, for example, stainless steel, a super elastic alloy such as Ni—Ti alloy, a shape memory alloy, a cobalt alloy, precious metals such as gold and platinum, metal materials such as tungsten alloy, or resin materials having at least a predetermined hardness.

The blunt needle hub 70 (rod member hub) holds the blunt needle 16 fixedly, and is accommodated in the housing 31 so as to be movable relative to the inner needle 14 and the inner needle hub 30. In the present embodiment, the blunt needle hub 70 engages with the catheter operation member 60, and the operating force, which may be an advancing force or a retracting force, is transmitted from the catheter operation member 60 to move the housing 31 in the distal direction or the proximal direction. At the time of movement of the blunt needle hub 70, the inner needle hub 30 (needle holding member 50) performs, with the structure described above, for example, guiding and limiting advancement and/or retraction of the needle hub 70. That is, the needle holding member 50 (inner needle hub 30), the catheter operation member 60, and the blunt needle hub 70 constitute the movement mechanism 17 for moving the blunt needle 16 along with the movement of the catheter 12.

Figure 7A:
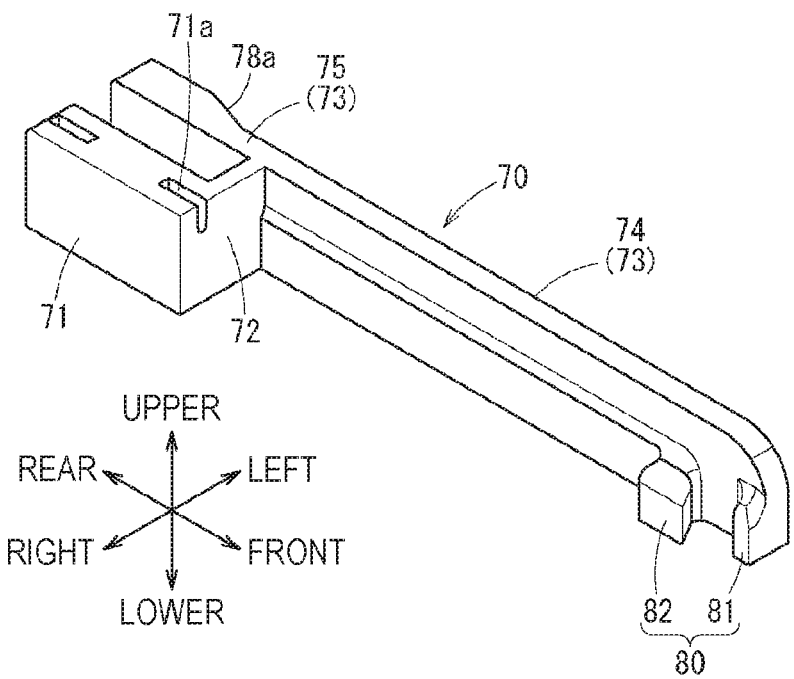
FIG. 7A is a perspective view illustrating the blunt needle hub of FIG. 1 in accordance with embodiments of the present disclosure.
Figure 7B:
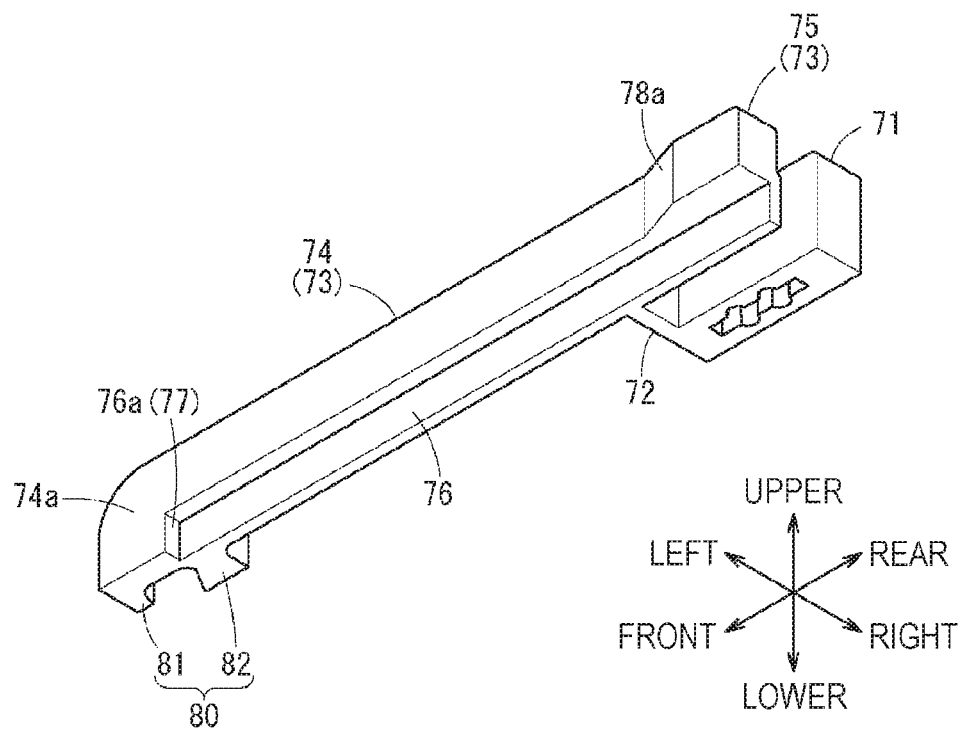
FIG. 7B is a perspective view of the blunt needle hub as viewed from the proximal end side thereof in accordance with embodiments of the present disclosure.

As illustrated in FIGS. 6, 7A, and 7B, the blunt needle hub 70 may be an integrally formed member of the holding portion 71, a hinge portion 72, and an arm portion 73, and may be disposed at an appropriate position of the needle holding member 50 in the pre-puncture state. A constituent material of the blunt needle hub 70 may be a resin material having an appropriate elastic force.

The holding portion 71 may be formed in a block shape (e.g., rectangular solid shape, etc.) which is long in the axial direction of the inner needle hub 30 and holds the proximal end side of the blunt needle 16. An attaching groove 71a may be formed at an upper corner in the center of the width of the distal end surface of the holding portion 71, and the blunt needle 16 may be fixed in the attaching groove 71a. In the assembled state of the catheter assembly 10, the distal end surface of the holding portion 71 may be disposed to face the proximal end surface of the holding body 56 (see also FIG. 8). In some embodiments, when the blunt needle hub 70 advances with respect to the needle holding member 50 and the distal end surface of the holding portion 71 contacts the proximal end surface of the holding body 56, the further advancement of the blunt needle hub 70 is prevented.

The hinge portion 72 protrudes from one side of the holding portion 71 in one width direction (direction orthogonal to the extending direction of the holding portion 71: to the left in the present embodiment), and functions as a base point of rotating the arm portion 73 relative to the holding portion 71. The hinge portion 72 may be continuous from the distal end surface of the holding portion 71, and may support a position slightly on the proximal end side from the longitudinally middle portion of the arm portion 73. The hinge portion 72 may be formed to be thin in the front-rear direction and at the same height as the height of the holding portion 71 in the vertical direction. In some embodiments, the hinge portion 72 may be configured as a living hinge comprising a thin section of material that connects the holding portion 71 to the arm portion 73. As the holding portion 71 is moved relative to the arm portion 73, the hinge portion 72 may flex, or bend, providing rotation therebetween.

The arm portion 73 has an inner side surface connected to the hinge portion 72, and extends in parallel to the holding portion 71 in the pre-puncture state. With the hinge portion 72 as a base point, the arm portion 73 has a distal end arm 74 extending sufficiently long in the distal direction and a proximal end arm 75 extending short in the proximal direction. The distal end arm 74 extends in the distal direction from the cover portion 55 of the needle holding member 50 in the pre-puncture state. The proximal end arm 75 extends to the same position as the proximal end of the holding portion 71.

A cutout 76 may be formed on the outside surface of the arm portion 73. The cutout 76 may be formed by removing a portion of material running along the lower corner of the arm portion 73, and extends from the proximal end toward the distal direction of the arm portion 73. The distal end of the cutout 76 reaches the vicinity of the engaging portion 80 of the arm portion 73, and a surface facing the cutout 76 is a surface to be limited 76a which is hooked on the retraction limiting surface 57a of the lower guide portion 57 of the needle holding member 50. That is, a retraction limiting mechanism 77 that limits the retraction of the blunt needle hub 70 is configured by the retraction limiting surface 57a of the needle holding member 50 and the surface to be limited 76a of the blunt needle hub 70.

Further, a protrusion 78 which protrudes outward in the width direction is provided on the outside surface of the arm portion 73 (proximal end arm 75). The protrusion 78 is located above the cutout 76 and faces the upper guide portion 58 of the needle holding member 50 in the pre-puncture state. Therefore, the protrusion 78 comes to contact with and is guided by the upper guide portion 58 during the movement of the blunt needle hub 70. The distal end side surface 74a of the cutout 76 of the arm portion 73 (distal end arm 74) comes into contact with and guides the lower guide portion 57 when the blunt needle hub 70 moves.

The protrusion 78 protrudes outward in a predetermined amount (in a range where it does not contact the side wall 33 of the housing 31). The distal end side of the protrusion 78 is a tapered surface 78a that is inclined toward the proximal end and outward.

On the other hand, the inner side surface of the arm portion 73 may be formed with an uneven shape in which the lower side slightly protrudes inward with respect to the upper side in accordance with the cutout 76 described above. That is, the lower side of the arm portion 73 may be formed to be thin corresponding to the thickness of the cutout 76, and can be directed farther inward than the upper side. In the vicinity of the distal end of the inside surface of the distal end arm 74, the engaging portion 80 that engages with the portion to be engaged 63 of the catheter operation member 60 in the pre-puncture state. The engaging portion 80 includes a first engaging projection 81 located at the distal end and a second engaging projection 82 located on the proximal end side of the first engaging projection 81.

The first engaging projection 81 projects a short distance inward from the distal end of the arm portion 73. The distal end surface of the first engaging projection 81 is formed flat in a direction perpendicular to the extending direction of the arm portion 73, while the proximal end surface of the first engaging projection 81 is formed in a curved surface extending obliquely and curved relative to the extending direction of the arm portion 73.

The second engaging projection 82 projects inward of the arm portion 73 at a position separated from the first engaging projection 81 by a predetermined distance (approximately equivalent to the thickness of the projection to be engaged 69). The second engaging projection 82 projects farther than the first engaging projection 81. Further, the distal end surface of the second engaging projection 82 is inclined relative to the extending direction of the arm portion 73, while the proximal end surface of the second engaging projection 82 is formed flat and extends orthogonally to the extending direction of the arm portion 73.

Figure 8:
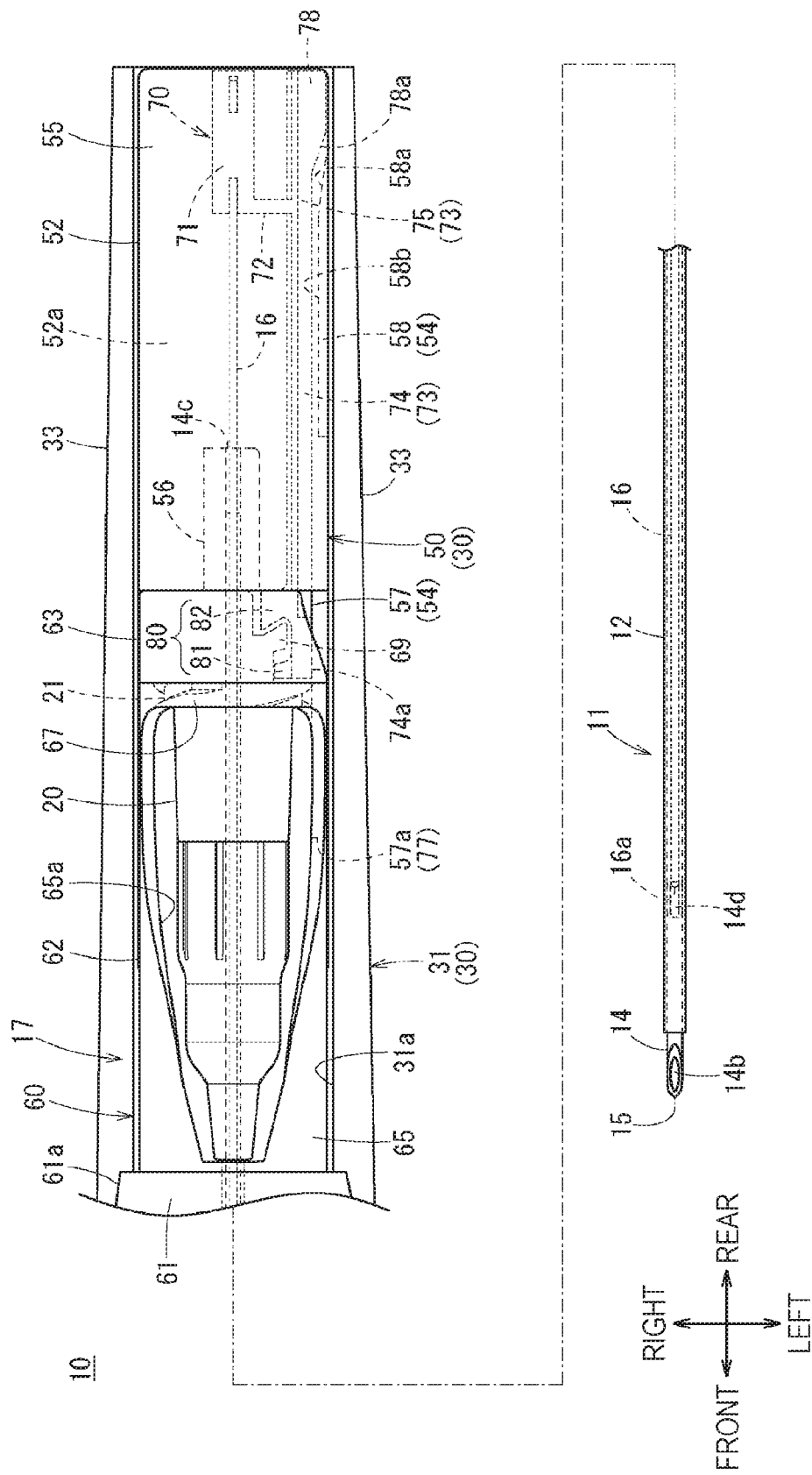
FIG. 8 is a plan view illustrating the catheter assembly of FIG. 1 in a pre-puncture state in accordance with embodiments of the present disclosure.

As illustrated in FIGS. 1, 3, and 8, the catheter assembly 10 appropriately assembles the above-described members to form the pre-puncture state. That is, the catheter hub 20, the support member 40, the needle holding member 50, the catheter operation member 60, and the blunt needle hub 70 are accommodated in the housing 31. The blunt needle 16 is inserted into the hollow portion 14a of the inner needle 14, and the inner needle 14 is inserted into the lumen 12a of the catheter 12 to form the multitube portion 11.

The needle holding member 50 is integrated into the inner needle hub 30 by mounting the mounting protrusions 51a in the mounting holes 36 of the housing 31. In this state, the proximal end of the housing 31 and the proximal end of the needle holding member 50 coincide with each other. The attaching space 52a of the frame structure 52 of the needle holding member 50 is located on the proximal end side of the inner needle hub 30.

In the housing 31, the catheter operation member 60 stores the catheter hub 20 in the hub storage portion 62 (holds the catheter hub 20 by the pair of side plates 66 and the arch portion 67), and is then disposed immediately before the distal end of the frame structure 52. The catheter operation member 60 can be advanced and retracted relative to the inner needle hub 30, as the pair of side edges 61a of the catheter operation member 60 is inserted into the pair of rail portions 37 of the housing 31.

A major part of the blunt needle hub 70 is accommodated in the attaching space 52a of the needle holding member 50, while the engaging portion 80 of the arm portion 73 (the proximal arm 74) protruding from the attaching space 52a is engaged with the portion to be engaged 63 of the catheter operation member 60. In this case, the first engaging projection 81 of the engaging portion 80 is positioned on the distal end side of the projection to be engaged 69 of the portion to be engaged 63, and the second engaging projection 82 of the engaging portion 80 is positioned on the proximal end side of the projection to be engaged 69.

Further, in the pre-puncture state, the arm portion 73 of the blunt needle hub 70 extends parallel to the blunt needle 16 and the holding portion 71. The protrusion 78 of the blunt needle hub 70 is on the proximal end side of the upper guide portion 58 of the needle holding member 50 and does not contact the upper guide portion 58. The holding portion 71 of the blunt needle hub 70 faces the holding body 56 of the needle holding member 50 and holds the blunt needle 16.

The blunt needle 16 linearly extending from the holding portion 71 is inserted into the hollow portion 14a of the inner needle 14 and extends inside the inner needle 14. The distal end of the blunt needle 16 is located on the proximal end side of the hole 14d of the inner needle 14.

The catheter assembly 10 according to the present embodiment may be configured as described above, and the operation and effects of the catheter assembly 10 are described below in accordance with embodiments of the present disclosure.

The catheter assembly 10 is used in building the introducer for infusion on the body of the patient, as described above. Before puncture, the user optionally rotates the catheter hub 20 relatively in order to eliminate adhesion between the catheter 12 and the inner needle 14. At this time, with the catheter assembly 10, it is possible to rotate the catheter hub 20 easily, because the blunt needle hub 70 is engaged with the catheter operation member 60.

In use, the user grips the housing 31 to puncture the multitube portion 11 into the patient. In the pre-puncture state, the distal end surface 16a of the blunt needle 16 is located on the proximal end side of the hole 14d. During puncture, therefore, the blood that has flowed into the hollow portion 14a of the inner needle 14 passes through the hole 14d and flows into the lumen 12a of the catheter 12. That is, the user can confirm whether the blood flashback is visible via the hole 14d to check that the blood vessel has been properly located and pierced.

In the puncturing state of the multitube portion 11, as illustrated in FIG. 2A, the user performs an initial advancement of the catheter (advancing operation of the catheter operation member 60) to advance the catheter 12 beyond the inner needle 14 and insert the catheter 12 into the blood vessel. At this time, as the catheter operation member 60 advances, the blunt needle hub 70 engaged with the catheter operation member 60 moves forward. Specifically, the projection to be engaged 69 is hooked on the first engaging projection 81 of the blunt needle hub 70 and pulls the arm portion 73. Further, the catheter hub 20 stored in the hub storage portion 62 advances along with the sliding of the catheter operation member 60. Accordingly, the catheter 12 fixed to the catheter hub 20 and the blunt needle 16 fixed to the blunt needle hub 70 advance relative to the inner needle 14.

Here, in the pre-puncture state, the protrusion 78 of the blunt needle hub 70 is located spaced apart from the proximal end side of the upper guide portion 58 of the needle holding member 50. Therefore, although the initial stage is the hardest (heaviest) operation in advancing the catheter operation member 60, the needle holding member 50 hardly hinders the movement of the blunt needle hub 70 and enables the advancement smoothly with the catheter assembly 10.

When it is desired to pull back the catheter 12 inserted into the blood vessel, the user performs a retracting operation of the catheter operation member 60. At this time, as the catheter operation member 60 retracts, the blunt needle hub 70 engaged with the catheter operation member 60 moves rearward. Specifically, when the projection to be engaged 69 of the catheter operation member 60 is hooked on the second engaging projection 82 of the blunt needle hub 70 and pushed in the proximal direction, the blunt needle hub 70 is also retracted. Thus, the catheter 12 and blunt needle 16 retract relative to inner needle 14.

Figure 9:
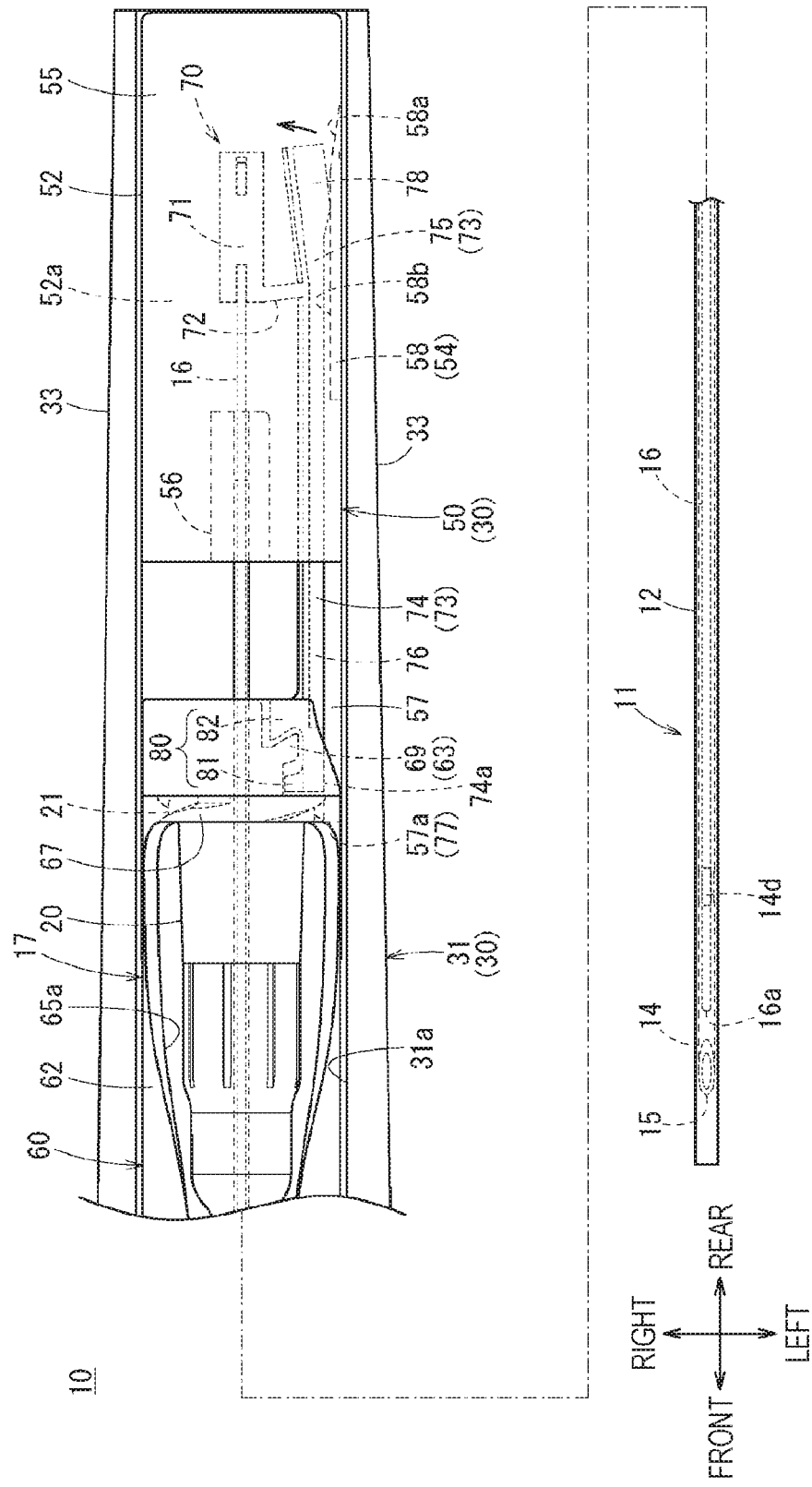
FIG. 9 is a plan view illustrating an operation during an initial advancement of the catheter assembly of FIG. 8.

As illustrated in FIG. 9, the catheter operation member 60 is moved in the distal direction in the catheter assembly 10, and the protrusion 78 is moved in the direction perpendicular to the axial direction of the blunt needle 16 by the needle holding member 50. Specifically, when the catheter operation member 60 slightly advances in the distal direction, the protrusion 78 (tapered surface 78a) of the blunt needle hub 70 is guided by the inclined surface 58a of the upper guide portion 58. Therefore, the protrusion 78 is directed inward. On the other hand, the blunt needle hub 70 moves forward while maintaining the engagement with the catheter operation member 60 by the catheter operation member 60 moving in the distal direction. Specifically, the distal end side surface 74*a* of the distal end arm 74 contacts the lower guide portion 57 to guide the advancement, and keeps the portion to be engaged 63 engaged by the engaging portion 80.

Therefore, the proximal end arm 75 on the proximal end side of the hinge portion 72 of the blunt needle hub 70 is elastically deformed as a whole to store a spring force (a force for moving the engaging portion 80). In particular, at the stage when the protrusion 78 reaches the flat surface 58*b* of the upper guide portion 58, the proximal end arm 75 is largely curved and is in a state of being close to the holding portion 71. In the movement stage in FIG. 9, the blunt needle 16 passes the hole 14*d* of the inner needle 14 and reaches near the needle tip 15 (proximal to the needle tip 15).

Figure 10:
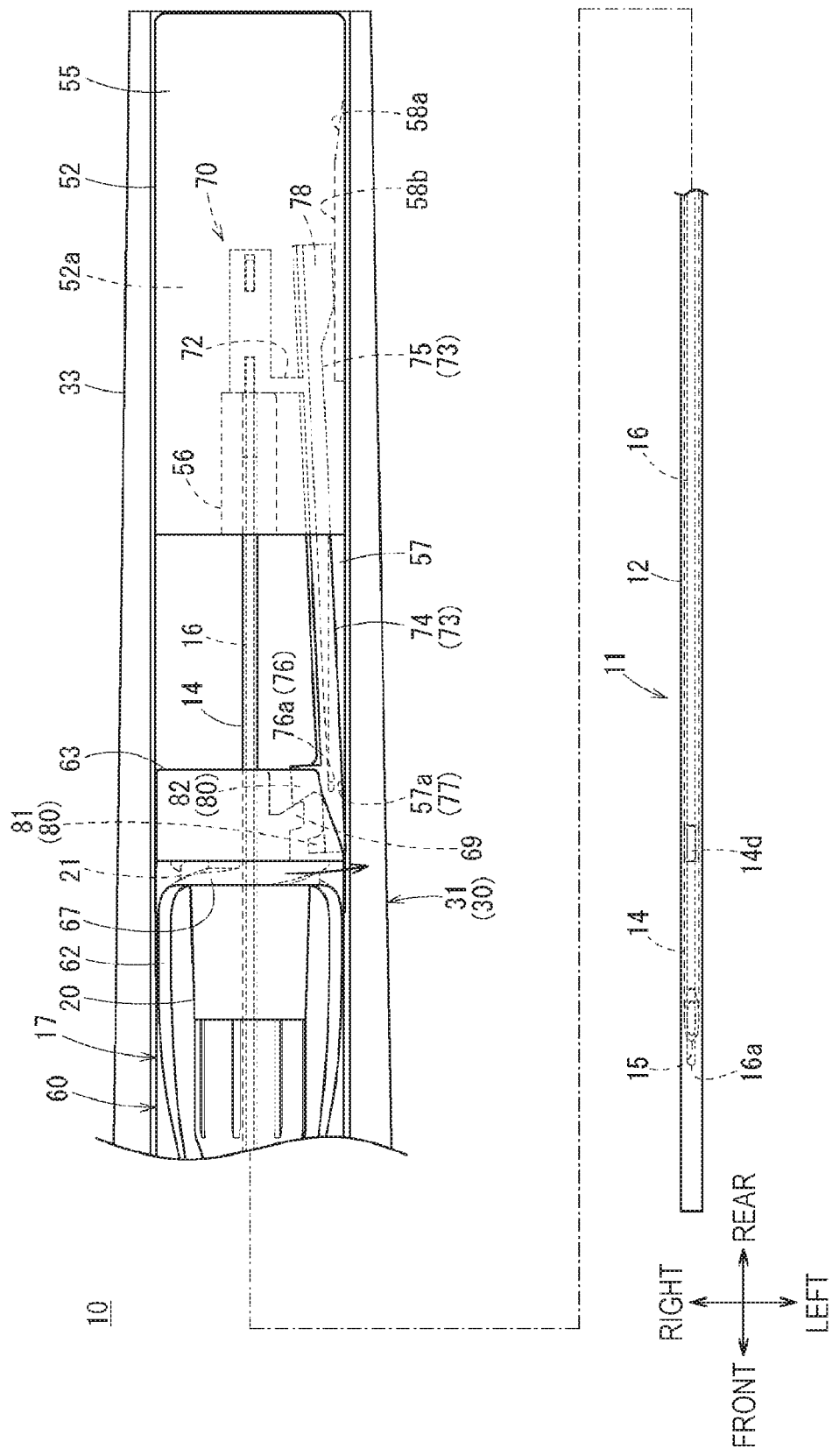
FIG. 10 is a plan view illustrating an operation during an initial advancement following the operation shown in FIG. 9.

When the advancement of the catheter operation member 60 is further continued, the cutout 76 of the arm portion 73 reaches the distal end of the lower guide portion 57 of the needle holding member 50, as illustrated in FIG. 10. That is, the distal end side surface 74*a* is disengaged from the guide of the lower guide portion 57. Then, due to the deformation of the protrusion 78 in the direction orthogonal to the axial direction of the blunt needle 16, a force that moves the distal end arm 74 in the direction opposite to the direction acts. Specifically, as described above, due to the elastic deformation in the inward direction of the protrusion 78, the force of moving the distal end arm 74 of the arm portion 73 in the outward direction with the hinge portion 72 as a base point is increased. Therefore, the distal end of the distal end arm 74 opens in the outward direction while inserting the lower guide portion 57 into the cutout 76.

Thus, when the distal end arm 74 moves in the direction opposite to the direction orthogonal to the axial direction of the blunt needle 16, the engagement of the blunt needle hub 70 and the catheter operation member 60 is released. That is, when the distal end arm 74 opens outward, the engagement between the first engaging projection 81 and the projection to be engaged 69 is released. Thus, the catheter operation member 60 is disengaged from the blunt needle hub 70 when the user performs the advancing operation, and the catheter 12 and the catheter hub 20 are advanced. On the other hand, the blunt needle 16 and the blunt needle hub 70 are left on the proximal end side of the holding body 56 of the needle holding member 50.

Further, at the position where the engagement is released, the distal end of the blunt needle 16 is in a state of protruding from the needle tip 15 of the inner needle 14. That is, the catheter assembly 10 is configured such that the engagement between the catheter operation member 60 and the blunt needle hub 70 is released at the position where the distal end of the blunt needle 16 protrudes from the needle tip 15 of the inner needle 14. The catheter 12 that has advanced beyond the needle tip 15 is supported by the blunt needle 16 to decrease the deflection or the like of the catheter 12 itself, and when the inner needle 14 is advanced with respect to the catheter 12, the outer needle pricking with the needle tip 15 can be prevented.

In the projecting state, the distal end of the arm portion 73 is kept displaced in the direction orthogonal to the axial direction of the blunt needle 16, and the blunt needle hub 70 is limited from being retracted by a part of the needle holding member 50. Specifically, the distal end of the arm portion 73 is left displaced outward in the width direction by the protrusion 78 and the upper guide portion 58. In this state, the surface to be limited 76*a* constituting the cutout 76 is hooked on the retraction limiting surface 57*a* at the distal end of the lower guide portion 57. As a result, the retraction of the blunt needle hub 70 is limited at the disengaging position. In addition, the movement of the blunt needle hub 70 in the distal direction is also prevented by the presence of the holding body 56 of the needle holding member 50 in front of the holding portion 71. Therefore, the blunt needle 16 can maintain the projecting state from the needle tip 15 well.

Thereafter, in the late stage, as described above, the catheter operation member 60 is exposed from the housing 31 (see FIG. 2B), and the catheter hub 20 is further separated from the blunt needle 16 (waste assembly 19). The user also indwells the indwelling assembly 18 in the patient by separating the catheter operation member 60 from the catheter hub 20 (see FIG. 2C).

Figure 11A:
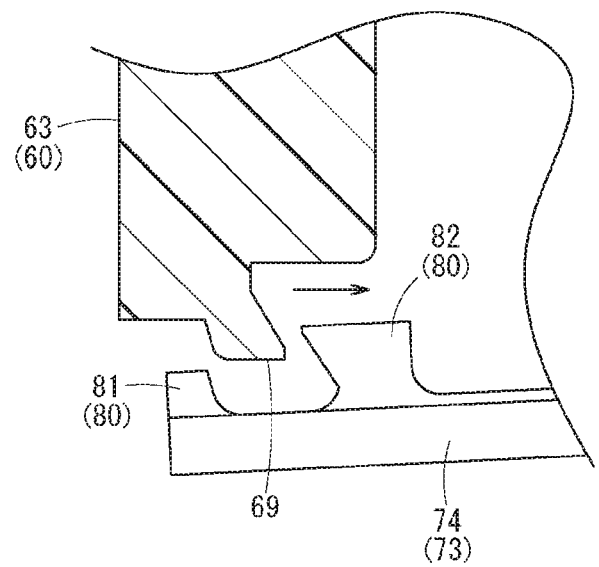
FIG. 11A is a detail section plan view illustrating an operation during retraction of the catheter operation member after disengagement in accordance with embodiments of the present disclosure.
Figure 11B:
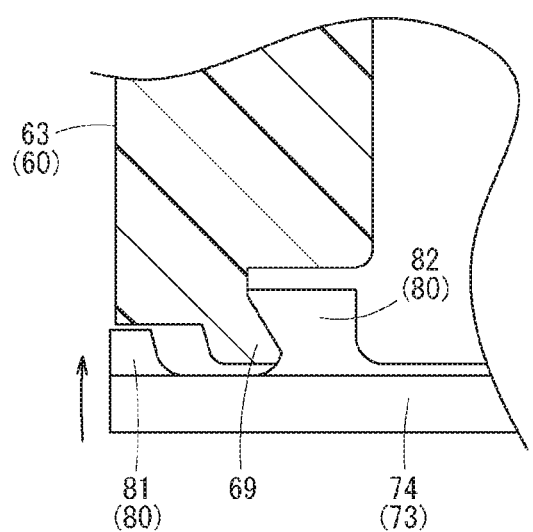
FIG. 11B is a detail section plan view illustrating an operation following the operation shown in FIG. 11A.

The catheter assembly 10 can reengage with the blunt needle hub 70 even when the catheter operation member 60 is retracted again after the disengagement position is exceeded. That is, even in the disengagement state of the catheter operation member 60 and the blunt needle hub 70, the second engaging projection 82 and the projection to be engaged 69 overlap each other in a front view of the catheter assembly 10. Therefore, as illustrated in FIG. 11A, when the catheter operation member 60 is retracted, the projection to be engaged 69 hooks the second engaging projection 82 and moves the distal end side of the arm portion 73 in the inward direction. Therefore, as illustrated in FIG. 11B, the retraction of the catheter operation member 60 restores the engagement between the engaging portion 80 and the portion to be engaged 63.

As described above, the catheter assembly 10 according to the first embodiment includes the blunt needle 16 and the movement mechanism 17 to allow the distal end of the blunt needle 16 to protrude beyond the needle tip 15 by the movement mechanism 17 when the catheter 12 is advanced and inserted into the blood vessel by the operation of the user. The blunt needle 16 protruding from the needle tip 15 can reliably prevent outer needle pricking or mispricking. In particular, the movement mechanism 17 has an excellent operability in that the movement mechanism 17 moves the blunt needle 16 along with the movement of the catheter 12 and does not separately request the user to perform the protruding operation. Further, the catheter hub 20 and the movement mechanism 17 are separate bodies, so that the catheter hub 20 can be configured to make the catheter 12 and the catheter hub 20 rotatable relative to the inner needle 14. This configuration may further prevent a damage or the like of the catheter hub 20. Thus, the safe handleability of the catheter assembly 10 may be greatly enhanced.

Meanwhile, the catheter assembly 10 uses the catheter operation member 60 (e.g., engagement member) and a blunt needle hub 70 (e.g., rod member hub) as the movement mechanism 17 for moving the blunt needle 16. Accordingly, when the catheter operation member 60 is moved, the rod member hub 70 engaged with the catheter operation member 60 moves, and the moving force can be easily applied to the blunt needle 16. Alternatively, as the engagement member engages with the catheter hub 20 to transmit force to the blunt needle hub 70, the movement mechanism 17 may be formed as a safety mechanism, a valve, or the like which is engaged with the catheter hub 20, or as a part of the inner needle hub 30 or the blunt needle hub 70 provided separately from the catheter hub 20. When the blunt needle 16 and the safety mechanism are combined, the catheter assembly 10 can further improve the mispricking preventing function and/or decrease the chance of blood exposure.

Further, the catheter assembly 10 can move the catheter operation member 60 and the blunt needle hub 70 together when the engaging portion 80 engages the portion to be engaged 63. Since the engagement is released at a position where the blunt needle 16 protrudes beyond the needle tip 15, the catheter 12 and the catheter hub 20 can be easily moved after the disengagement, and indwelled on the patient side. Further, the inner needle hub 30 regulates the retraction of the blunt needle hub 70 at the disengagement position, so that the retraction of the blunt needle 16 protruding from the needle tip 15 can be prevented easily and reliably.

Along with the advancement, the blunt needle hub 70 increases a spring force for moving the arm portion 73 in the direction of releasing the engagement between the engaging portion 80 and the portion to be engaged 63, thus allowing execution of the disengagement smoothly between the engaging portion 80 and the portion to be engaged 63 at a desired position. Further, along with the advancement of the blunt needle hub 70, the upper guide portion 58 of the inner needle hub 30 can easily increase the operating force in the direction of releasing the engagement between the engaging portion 80 and the portion to be engaged 63. In particular, the blunt needle hub 70 includes the holding portion 71, the hinge portion 72, and the arm portion 73, so that the blunt needle hub 70 can move the arm portion 73 using the hinge portion 72 as a base point. As the spring force increases by the upper guide portion 58 of the inner needle hub 30, the arm portion 73 can easily deform the engaging portion 80 in the outward direction in which the engagement is released.

In the catheter assembly 10, the first engaging projection 81 engages the projection to be engaged 69 at the time of advancing the catheter operation member 60, so that the blunt needle hub 70 can smoothly follow and advance. Further, the projection to be engaged 69 is engaged with the second engaging projection 82 when the catheter operation member 60 is retracted, so that the blunt needle hub 70 can be pushed in smoothly. Even when the engagement of the first engaging projection 81 and the projection to be engaged 69 is released, the second engaging projection 82 and the projection to be engaged 69 overlap in a front view of the catheter assembly 10. Therefore, when the operation member is retracted, the blunt needle hub 70 can follow and retract.

The catheter assembly 10 may adopt various applications and modifications. For example, the movement mechanism 17 of the blunt needle 16 is not limited to a structure in which the catheter operation member 60 and the blunt needle hub 70 are engaged and a moving force is applied from the catheter operation member 60. In another embodiment, the movement mechanism 17 may be attached to the proximal end of the catheter hub 20, while a valve mechanism (not illustrated) for closing the internal space of the catheter hub 20 may be provided with the projection to be engaged 69, thus engaging the engaging portion 80 of the blunt needle hub 70.

Other modifications to the embodiments disclosed herein are described below with reference to FIGS. 12A to 12D. In the following description, the constituent components having the same configuration or the same function as the components of the catheter assembly 10 according to the first embodiment are denoted by the same reference numerals, and the detailed description thereof is omitted.

Figure 12A:
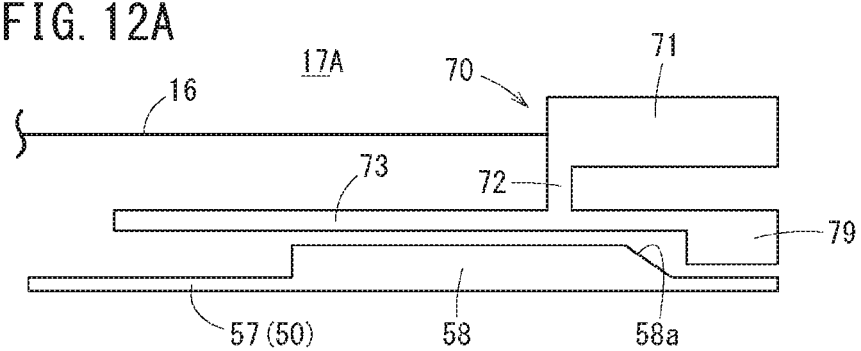
FIG. 12A is a schematic plan view of a movement mechanism according to a first modification in accordance with embodiments of the present disclosure.

In a movement mechanism 17A according to a first modification illustrated in FIG. 12A, a protrusion 79 of the blunt needle hub 70 is formed in a rectangular shape in a plan view, and only the upper guide portion 58 of the needle holding member 50 has the inclined surface 58a. In this configuration, when the blunt needle hub 70 advances, the corner of the protrusion 79 also strikes the inclined surface 58a and is elastically deformed in the inward direction.

Figure 12B:
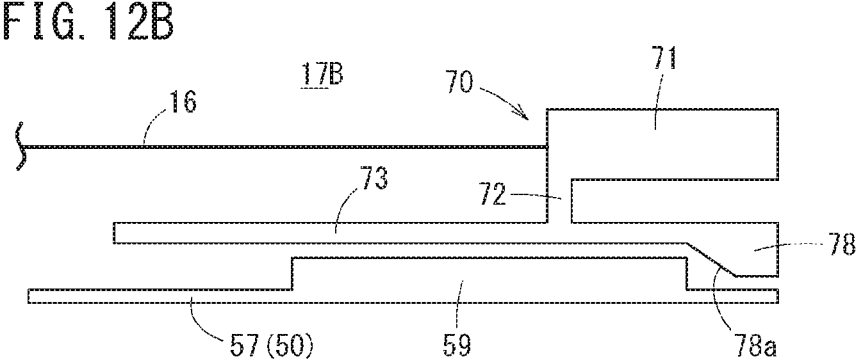
FIG. 12B is a schematic plan view of a movement mechanism according to a second modification in accordance with embodiments of the present disclosure.

Conversely, in a movement mechanism 17B according to a second modification illustrated in FIG. 12B, the distal end of the protrusion 78 of the blunt needle hub 70 may be formed on the tapered surface 78a, and an upper guide portion 59 of the needle holding member 50 may have a rectangular shape in plan view.

Figure 12C:
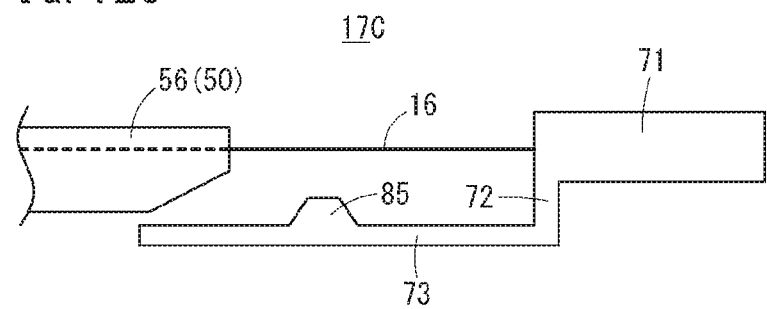
FIG. 12C is a schematic plan view of a movement mechanism according to a third modification in accordance with embodiments of the present disclosure.

A movement mechanism 17C according to a third modification illustrated in FIG. 12C has a protrusion 85 on the distal end side of the arm portion 73. Even when the protrusion 85 is provided on the distal end side of the arm portion 73, the protrusion 85 may contact, for example, the holding body 56 of the needle holding member 50 to displace the arm portion 73 outward.

Figure 12D:
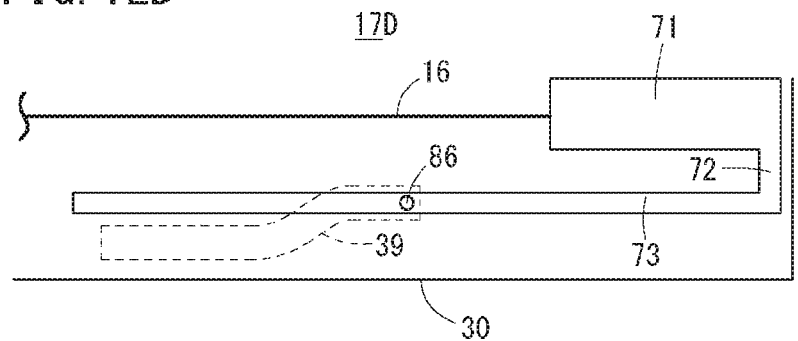
FIG. 12D is a schematic plan view of a movement mechanism according to a fourth modification in accordance with embodiments of the present disclosure.

Further, in a movement mechanism 17D according to a fourth modification illustrated in FIG. 12D, the hinge portion 72 is provided on the proximal end side of the holding portion 71, and the protrusion 78 is replaced by a guide pin 86 disposed at a predetermined position of the extended portion of the arm portion 73. The inner needle hub 30 has a pin groove 39 for guiding the guide pin 86. The pin groove 39 is configured to guide the distal end of the arm portion 73 to be displaced outward.

In short, the shapes, positions, and the like of the hinge portion 72 and the arm portion 73 of the blunt needle hub 70 are not particularly limited to the embodiments and/or modifications described herein as long as the engaging portion 80 of the arm portion 73 can be engaged/disengaged. Further, the shape of the inner needle hub 30 for guiding the deformation of the blunt needle hub 70 may be appropriately configured in accordance with the blunt needle hub 70.

Second Embodiment

Figure 13A:
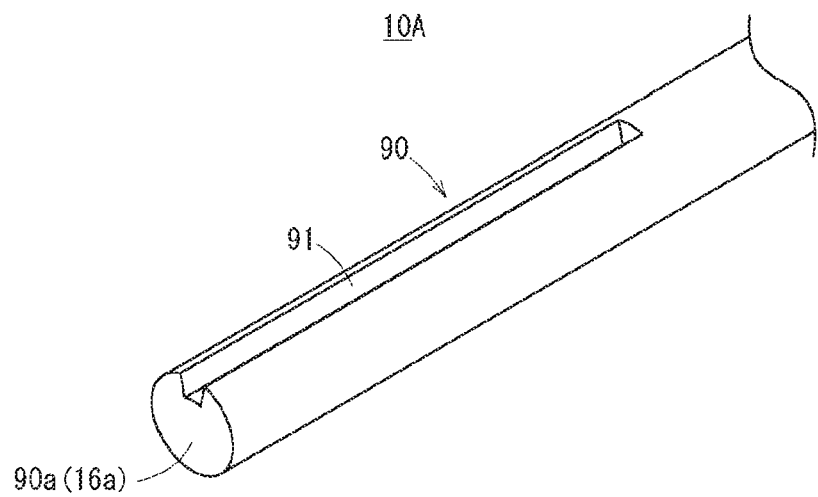
FIG. 13A is a perspective view illustrating a first shape of a distal end region of a blunt needle of a catheter assembly according to a second embodiment of the present disclosure.

A catheter assembly 10A according to a second embodiment differs from the blunt needle 16 of the catheter assembly 10 according to the first embodiment in the shape of the distal end region of a blunt needle 90, as illustrated in FIG. 13A. The configuration other than the blunt needle 90 is similar, if not identical, to that of the catheter assembly 10 described above.

In this case, the blunt needle 90 has a concave groove portion 91 extending a predetermined length in the proximal direction from the distal end surface 90a. The concave groove portion 91 functions as a flowing channel for flowing blood through the inner needle 14. For example, the concave groove portion 91 is formed by cutting out a range (e.g., of about ¼ to ⅛ of the peripheral length) of the entire circumference of the blunt needle 90 toward the inside with a depth of a groom bottom not reaching the central axis.

Figure 14A:
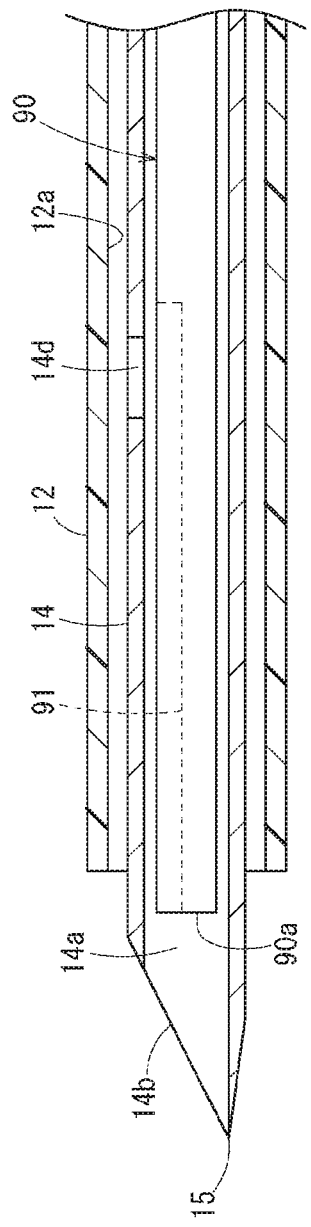
FIG. 14A is a side sectional view illustrating the multitube portion of the catheter assembly of FIG. 13A in a pre-puncture state in accordance with embodiments of the present disclosure.

As illustrated in FIG. 14A, the distal end surface 90a of the blunt needle 90 is located in the vicinity of the distal end opening 14b of the inner needle 14 (at a position slightly closer to the proximal end than to the distal end opening 14b) in a state accommodated in the hollow portion 14a of the inner needle 14 in the pre-puncture state. In some embodiments, the distal end surface 90a of the blunt needle 90 is located on (or coincide with) the distal end side of the distal end position of the catheter 12. The concave groove portion 91 of the blunt needle 90 is formed in a range from the distal end surface 90a to the proximal end side of the hole 14d of the inner needle 14 in the pre-puncture state.

With the blunt needle 90 formed as described above, the blood can be guided to flow from the distal end opening 14b through the concave groove portion 91 and to the hole 14d in a state where the blood vessel is punctured with the multitube portion 11. Therefore, the blood flows in the lumen 12a of the catheter 12 through the hole 14d, so that the user can confirm the flashback.

Figure 14B:
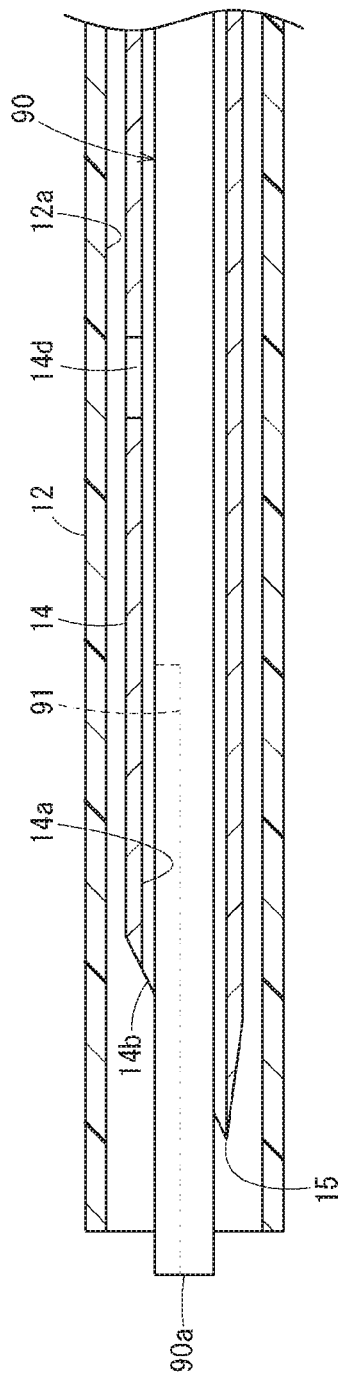
FIG. 14B is a side sectional view illustrating the operation of the catheter assembly of FIG. 13A in accordance with embodiments of the present disclosure.

Further, as illustrated in FIG. 14B, the blunt needle 90 is advanced by the movement mechanism 17 and immediately delivered to the distal end side of the needle tip 15 of the inner needle 14. This allows early prevention of the outer needle pricking by the inner needle 14 in the initial stage of movement of the catheter 12. Further, the blunt needle 90 is provided with the concave groove portion 91 only partially in the circumferential direction, leaving the distal end in a sufficiently blunt shape, so that it is possible to prevent the outer needle pricking and mispricking.

Figure 13B:
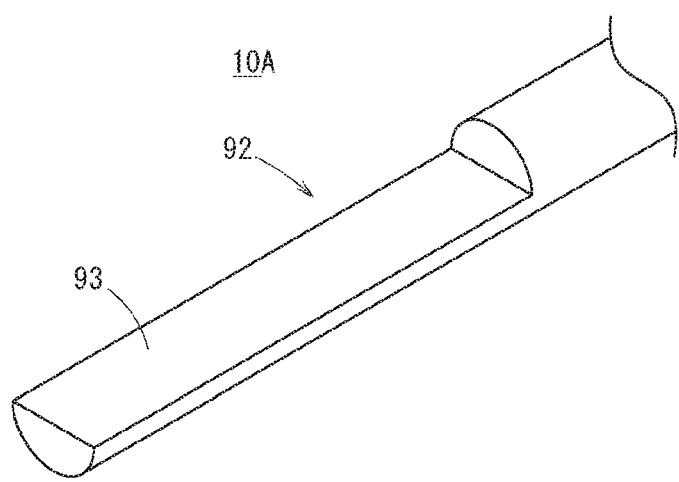
FIG. 13B is a perspective view illustrating a second shape of a distal end region of a blunt needle in accordance with embodiments of the present disclosure.

The flowing channel of the blood provided in the blunt needle 90 is not limited to the concave groove portion 91, and various shapes may be used. For example, as illustrated to FIG. 13B, the semicircular cutout part 93 in which the half the circumference of the blunt needle 92 may be cut out.

Third Embodiment

As illustrated in FIG. 15, a catheter assembly 10B according to a third embodiment of the present disclosure differs from the catheter assembly 10 or 10A in that a blunt needle hub 95 slidably inserts the blunt needle 16 extending in the proximal direction from the inner needle 14, and includes a folded portion 96 which is folded back toward the distal end. The catheter assembly 10B can increase the amount of movement of the distal end of the blunt needle 16 by having the folded portion 96.

Specifically, the holding portion 71 of the blunt needle hub 70 is formed in a large block shape in the width direction, and a passage 97 functioning as a folded portion 96 is formed inside the holding portion 71. Openings 97a and 97b at both ends of the passage 97 are connected to the distal end surface of the holding portion 71, and one opening 97a faces the proximal end opening 14c of the inner needle 14 held by the needle holding member 50 in the pre-puncture state. Thus, the blunt needle 16 extends linearly between the proximal end opening 14c of the inner needle 14 and the opening 97a of the passage 97.

In a plan view, the passage 97 is formed to extend from the one opening 97a in the proximal direction and then bent 180 degrees in an ending portion 97c to reach the other opening 97b. Therefore, the blunt needle 16 inserted into the passage 97 is folded back slidably between the one opening 97a and the other opening 97b according to the shape of the passage 97.

Further, the inner needle hub 30 is provided with a fixing portion 98 for fixing the ends of the blunt needle 16 (the distal end and the opposite end of the blunt needle 16). The blunt needle 16 delivered from the other opening 97b of the holding portion 71 extends in the axial direction of the housing 31 and is fixed at the fixing portion 98.

The catheter assembly 10B configured as described above enables the folded portion 96 itself to be advanced along with the advancement of the blunt needle hub 95 by the movement mechanism 17. In this case, the opposite end of the blunt needle 16 fixed at the fixing portion 98 is unmovable, so that the portion extending in the proximal direction from the fixing portion 98 enters the folded portion 96 (passage 97). On the other hand, the portion extending in the distal direction from the opening 97a is pushed by the holding portion 71 and moved in the distal direction. That is, by adding the folded portion 96 extending in the proximal direction to the blunt needle 16, the distal end of the blunt needle 16 can be advanced farther than the advancing amount of the blunt needle hub 70.

For example, as illustrated in the upper part of FIG. 16, it is assumed that the distal end of the blunt needle 16 moving in the inner needle 14 is substantially at the same position as the distal end of the catheter 12. When the blunt needle 16 is advanced by the movement mechanism 17, as illustrated in the lower part of FIG. 16, the distal end of the blunt needle 16 is advanced twice as much as the advancing amount of the distal end of the catheter 12. Thus, even when the blunt needle 16 is disposed somewhat closer to the proximal end side than the needle tip 15 of the inner needle 14 in the pre-puncture state, the folded portion 96 allows the blunt needle 16 to be delivered early from the inner needle 14, thus favorably prevent the outer needle pricking. A plurality of folded portions 96 may be provided on the blunt needle hub 70 and the inner needle hub 30, so that the advancing amount of the blunt needle 16 can be increased according to the plurality of folded portions 96, that is, increased threefold, fourfold, fivefold, and so on.

Fourth Embodiment

A catheter assembly 10C according to a fourth embodiment illustrated in FIG. 17 differs from the catheter assembly 10, 10A, or 10B in that a hard portion 101 whose entire length is formed by a blunt needle 100 and a soft portion 102 provided at the distal end of the hard portion 101 and is softer than the hard portion 101.

The hard portion 101 may be made of a constituent material listed in connection with the blunt needle 16 described above. In some embodiments, the soft portion 102 is made of an appropriate material softer than the material of the hard portion 101 and, for example, a material such as a metal material such as a nickel-titanium alloy or a resin material such as polyurethane can be used. The shape of the soft portion 102 can be changed to be flexible and, for example, coiled, twisted by a plurality of wires, having a non-circular cross-sectional shape, or having a small diameter. The total length of the soft portion 102 is not particularly limited, and may be in the range of, for example, 0.3 mm to 2.0 mm.

The blunt needle 100 includes the soft portion 102 disposed at the distal end of the hard portion 101, whereby the blunt needle 100 can be used flexibly without trouble even when the blunt needle 100 touches the catheter 12, the patient, the user, or the third person and can favorably prevent the outer needle pricking or mispricking. Further, the distal end portion of the soft portion 102 is formed in a semicircle shape in which the corner portion is scraped, whereby the blunt needle 100 can further prevent the outer needle pricking or mispricking more reliably.

In particular, it is assumed that the blunt needle 100 is arranged in a manner that the soft portion 102 is entirely disposed from the needle tip 15 of the inner needle 14, that is, the distal end of the hard portion 101 protrudes beyond the needle tip 15, at the position where the retraction of the blunt needle hub 70 is limited (at the engagement release position of the engaging portion 80 and the portion to be engaged 63). Accordingly, if the soft portion 102 on the distal end side is curved or the like, the hard portion 101 protruding from the needle tip 15 can prevent the mispricking.

The present disclosure is not limited to the above-described embodiment, and various modifications can be made along the subject matter of the disclosure.

Experiments

Experiments were carried out to verify the effect of the blunt needle 16 according to the first embodiment and the blunt needle 100 according to the fourth embodiment. In the experiments, first to fifth samples illustrated in FIG. 18 were prepared for comparison.

First Sample: The catheter 12, the inner needle 14, and the blunt needle 16 according to the first embodiment were used. The inner diameter of the inner needle 14 was 0.395 mm, and the outer diameter of the blunt needle 16 was 0.377 mm. Further, as described above, the needle tip 15 of the inner needle 14 was in the back-cut shape, the length of the back-cut was 0.035 mm, and the height of the back-cut was 0.029 mm. The outer diameter of the catheter 12 was 20G (e.g., approximately 1.1 mm).

Second Sample: The catheter 12, the inner needle 14, and the blunt needle 100 (having the hard portion 101 and the soft portion 102) according to the fourth embodiment were used. The inner diameter of the inner needle 14 was 0.395 mm, and the outer diameter of the blunt needle 16 was 0.376 mm. The needle tip 15 of the inner needle 14 was formed in a back-cut shape different from that of the first sample, the length of the back-cut was 0.105 mm, and the height of the back-cut was 0.087 mm. The outer diameter of the catheter 12 was 20G (e.g., approximately 1.1 mm).

Third Sample: An inner needle and a blunt needle different from the first and second samples were used. Specifically, the inner diameter of the inner needle was 0.595 mm, and the inner needle was formed in a lancet shape. The blunt needle was formed in a flat and non-circular shape by partially cutting out the circumference of the circular cross-section. In this case, the outer diameter from the flat surface to the arc surface opposite to the flat surface was 0.237 mm, and the outer diameter in the direction parallel to the flat surface was 0.385 mm. The outer diameter of the catheter 12 was 20G (e.g., approximately 1.1 mm).

Fourth Sample: An inner needle and a blunt needle different from those of the first to third samples were used. Specifically, the inner diameter of the inner needle was 0.442 mm, the back-cut length was 0.107 mm, and the back-cut height was 0.083 mm. A guide wire was used instead of the blunt needle, and the outer diameter of the guide wire was 0.357 mm. In this case, the protruding length of the guide wire from the inner needle was sufficiently longer than the protruding length of each blunt needle of the first to third samples. The outer diameter of the catheter 12 was 20G (e.g., approximately 1.1 mm).

Fifth Sample: An inner needle and a blunt needle different from the first to fourth samples were used. Specifically, the inner needle had an inner diameter of 0.598 mm and was formed in a lancet shape. A guide wire is used instead of the blunt needle, and the outer diameter of the guide wire was 0.453 mm. In addition, the protruding length of the guide wire from the inner needle is sufficiently longer than the protruding length of each blunt needle of the first to third samples. Further, the outer diameter of the catheter 12 is 16G (e.g., approximately 1.8 mm).

Figure 19:
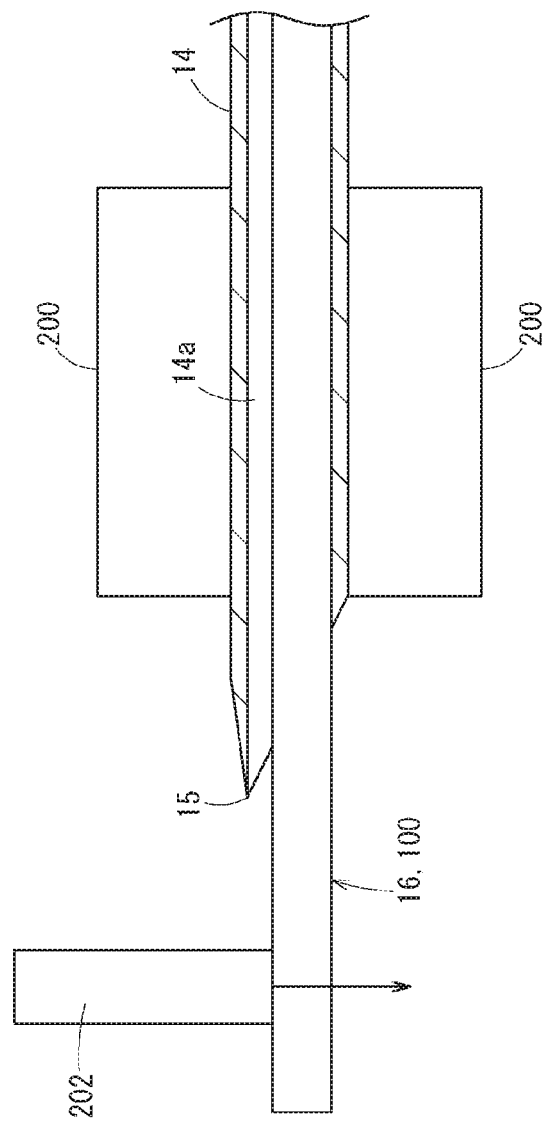
FIG. 19 is a schematic section view for explaining a first experiment of FIG. 18 in accordance with embodiments of the present disclosure.

As a first experiment, as illustrated in FIG. 19, the inner needle 14 (the reference numbers of the first embodiment are used representatively in all embodiments described herein unless otherwise indicated) of each sample was fixed by a needle fixing jig 200 with the blade surface facing downward. In the fixed state, the distal end of the needle fixing jig 200 is disposed so as to coincide with the proximal end of the blade surface. Then, the members of each sample (the first sample blunt needle 16, the second sample blunt needle 100, the third sample blunt needle, the fourth sample guide wire, and the fifth sample guide wire) were protruded from the inner needle 14. Further, the protrusion of each sample member was pushed by a pushing member 202. The pushing member 202 was configured to push each sample member at a constant speed at a position 2 mm away from the distal end of the inner needle 14 (needle tip 15), and the indentation force was able to be measured by a sensor not illustrated. Subsequently, the indentation strength was calculated by the indentation force per predetermined indentation amount.

The indentation strengths (e.g., the pressing strength, measured in N/mm) of the first to fifth samples are illustrated in FIG. 18. As can be seen from the first experimental result, the first and second samples had higher indentation strength values than the other third to fifth samples. In particular, the second sample was the blunt needle 100 having the hard portion 101 and the soft portion 102, but the same indentation strength as that of the first sample can be obtained by the hard portion 101 protruding from the inner needle 14.

Figure 20A:
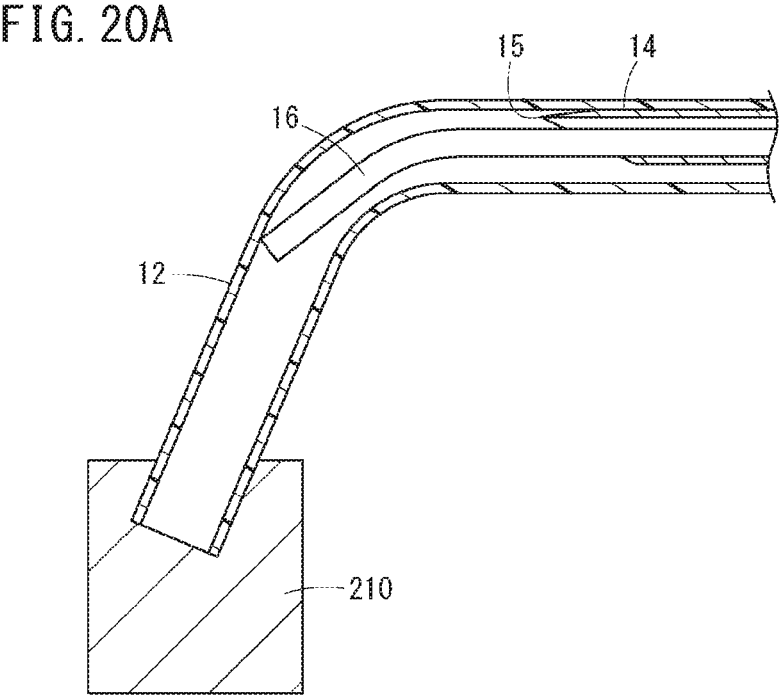
FIG. 20A is a schematic section view for explaining a second experiment of FIG. 18 in accordance with embodiments of the present disclosure.

As a second experiment, as illustrated in FIG. 20A, a weight 210 (e.g., measured in grams) was attached at a position 1 cm from the distal end of the catheter 12 in a state where the catheter 12 and the other sample members were protruding from the inner needle 14. With the blade surface of the inner needle 14 directed vertically downward, the catheter 12 was retracted and advanced back and forth while the posture of the inner needle 14 being adjusted so that the needle tip 15 of the inner needle 14 was horizontal. When the catheter 12 was able to move smoothly, the weight 210 was increased by 3 grams at the maximum, and the same experiment was repeated. On the other hand, when the catheter 12 stopped moving, the experiment of the sample was ended. The state in which the catheter 12 stops moving can be regarded as the state in which the catheter 12 is pierced by the inner needle 14 or the blunt needle 16.

The weight of the weight 210 at which the catheter 12 stopped moving is illustrated in FIG. 18. As can be seen from the result of the second experiment, the first sample stopped moving at 40.77 grams and the second sample at 84.42 grams, while the third sample stopped moving at 13.17 grams, the fourth sample at 10.38 grams, and the fifth sample at 17.50 grams. Therefore, it can be concluded that the first and second samples can significantly decrease the piercing of the inner needle 14 into the catheter 12 as compared to other samples. That is, the blunt needles 16 and 100 do not allow the inner needle 14 to pierce the catheter 12, even when the blunt needles 16 and 100 and the catheter 12 are protruded from the inner needle 14 and the catheter 12 is advanced and retracted with the weight 210 of 30 grams being attached to the distal end of the catheter 12, with the needle tip 15 being horizontal and the blade surface of the inner needle 14 being directed vertically downward.

Figure 20B:
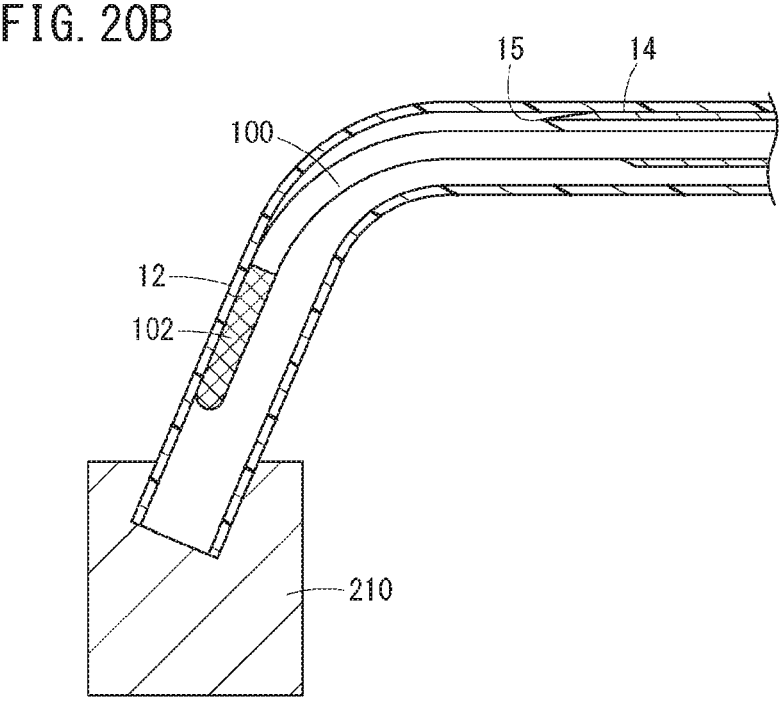
FIG. 20B is a schematic section view for explaining the state of the blunt needle of the fourth embodiment of the present disclosure in the second experiment of FIG. 18.

For the first sample member (the blunt needle 16), the catheter 12 stopped moving at 40.77 grams of the weight 210 by the resistance of the blunt needle 16 hitting the catheter 12 (see FIG. 20A). In contrast, as illustrated in FIG. 20B, the second sample member (blunt needle 100) was able to support the catheter 12 until the inner needle 14 pierces the catheter 12, because the soft portion 102 bent according to the catheter 12 so that the blunt needle 100 was not able to pierce the catheter 12. As a result, it can be considered that the weight of the weight 210 of the second sample was increased to 84.42 grams.

What is claimed is:

1. A catheter assembly, comprising:
   a catheter;
   a catheter hub fixedly holding the catheter;
   an inner needle having a needle tip and releasably inserted into the catheter;
   an inner needle hub fixedly holding the inner needle;
   a rod member disposed in a hollow portion axially extending in the inner needle and having a distal end portion blunter than the needle tip; and
   a movement mechanism that moves the rod member inside the inner needle, wherein the movement mechanism is formed separately from the catheter hub, causes a distal end of the rod member to protrude beyond the needle tip along with a movement of the catheter, and comprises:
      a rod member hub for applying a force to move the rod member; and
      an engagement member for engaging the catheter hub and the rod member hub,
      wherein the engagement member is an operation member that is formed separately from the inner needle hub, is detachably attached to the catheter hub, is able to operate a movement of the catheter hub, and moves the rod member along with the movement of the catheter hub,
      wherein the rod member hub comprises an engaging portion at a predetermined position,
      wherein the operation member has a portion to be engaged that engages with the engaging portion,
      wherein the portion to be engaged comprises a projection to be engaged, and
      wherein the projection to be engaged projects in a direction perpendicular to a moving direction of the operation member.

2. The catheter assembly of claim 1, wherein the inner needle hub includes a retraction limiting portion which limits retraction of the rod member relative to the inner needle by hooking the rod member hub at a position where an engagement of the engaging portion and the portion to be engaged is released.

3. The catheter assembly of claim 1, wherein the rod member hub receives the force to move the rod member hub in a direction in which an engagement of the engaging portion and the portion to be engaged is released along with an advancement of the rod member hub relative to the inner needle.

4. The catheter assembly of claim 3, wherein the inner needle hub includes a guide portion that increases the force to move the rod member hub along with the advancement of the rod member hub.

5. The catheter assembly of claim 4, wherein the rod member hub comprises:
   a holding portion for holding the rod member,
   a hinge portion continuous with the holding portion and projecting in a direction perpendicular to an extending direction of the holding portion, and
   an arm portion continuous with the hinge portion, having the engaging portion at a distal end side of the arm portion, and extending in parallel with the holding portion in a pre-puncture state of the catheter assembly,
   the arm portion includes a protrusion on a proximal end side of the arm portion,
   the protrusion increasing the force to move the rod member hub inward from the inner needle hub when guided by the guide portion along with the advancement of the rod member hub, and
   the engaging portion moves in a lateral direction of the inner needle hub by the force to move the rod member.

6. The catheter assembly of claim 1, wherein the rod member hub includes at least one folded portion that slidably inserts into the rod member that extends in a proximal direction of the catheter assembly from the inner needle and folded back in a distal direction of the catheter assembly.

7. The catheter assembly of claim 1, wherein the distal end of the rod member is located on a proximal side of a hole communicating an outside of the inner needle with the hollow portion about the catheter and the inner needle in a pre-puncture state of the catheter assembly.

8. The catheter assembly of claim 1, wherein the distal end of the rod member is located on a distal side of a hole communicating an outside of the inner needle with the hollow portion about the catheter and the inner needle in a pre-puncture state of the catheter assembly, and the rod member includes a flowing channel in a range from at least the distal end of the rod member to the hole.

9. The catheter assembly according to claim 1, wherein the rod member comprises a protruding portion protruding from the inner needle, the protruding portion of the rod member comprising a hard portion on a proximal end side of a protrusion and a soft portion on a distal end side of the protrusion, the soft portion being softer than the hard portion.

10. The catheter assembly of claim 1, wherein the inner needle includes a blade surface, and the rod member prevents the catheter from piercing the rod member by the inner needle when the rod member and the catheter are made to protrude from the inner needle and the catheter is advanced and retracted, with a weight of 30 grams being attached to a distal end of the catheter, the needle tip being arranged horizontal, and the blade surface of the inner needle facing vertically downward.

11. The catheter assembly of claim 1, wherein the engaging portion comprises, in a pre-puncture state of the catheter assembly, a first engaging projection located on a distal end side of the projection to be engaged and capable of engaging the projection to be engaged.

12. The catheter assembly of claim 11, wherein the engaging portion further comprises a second engaging projection located on a proximal end side of the projection to be engaged and capable of engaging the projection to be engaged, and wherein the second engaging projection projects beyond the first engaging projection and, in a state where an engagement of the first engaging projection and the projection to be engaged is released, the projection to be engaged and the second engaging projection overlap in a front view of the catheter assembly.

13. A catheter assembly, comprising:
   a catheter;
   a catheter hub fixedly holding the catheter;
   an inner needle having a needle tip and releasably inserted into the catheter;
   an inner needle hub fixedly holding the inner needle;
   a rod member disposed in a hollow portion axially extending in the inner needle and having a distal end portion blunter than the needle tip;
   a movement mechanism that moves the rod member inside the inner needle, wherein the movement mechanism is formed separately from the catheter hub, and causes a distal end of the rod member to protrude beyond the needle tip along with a movement of the catheter, wherein the movement mechanism comprises:
a rod member hub for applying a force to move the rod member, and
an engagement member for engaging the catheter hub and the rod member hub, wherein the engagement member is an operation member which is detachably attached to the catheter hub, is able to operate a movement of the catheter hub, and moves the rod member along with the movement of the catheter hub;

wherein
the rod member hub is moveable relative to the inner needle, and has an engaging portion at a predetermined position,
the operation member has a portion to be engaged which is engaged with the engaging portion, and
the engaging portion and the portion to be engaged are maintained in an engagement of the catheter and the inner needle in a pre-puncture state of the catheter assembly and the inner needle, and released from the engagement of the catheter and the inner needle at a position where the rod member protrudes beyond the needle tip;

wherein the portion to be engaged has a projection to be engaged projecting in a direction perpendicular to a moving direction of the operation member,
the engaging portion includes, in the pre-puncture state of the catheter assembly and the inner needle, a first engaging projection located on a distal end side of the projection to be engaged and capable of engaging the projection to be engaged and a second engaging projection located on a proximal end side of the projection to be engaged and capable of engaging the projection to be engaged, and
the second engaging projection projects beyond the first engaging projection and, in a state where an engagement of the first engaging projection and the projection to be engaged is released, the projection to be engaged and the second engaging projection overlap in a front view of the catheter assembly.

14. A catheter assembly, comprising:
a catheter having a lumen running from a proximal end of the catheter to a distal end of the catheter;
a catheter hub fixedly attached to the proximal end of the catheter;
an inner needle disposed within a portion of the lumen, the inner needle comprising a sharpened tip at a distal end of the inner needle;
an inner needle hub fixedly attached to the inner needle at a proximal end of the inner needle;
a rod member slidably disposed within a hollow portion of the inner needle, wherein the rod member comprises a blunt end disposed adjacent to the sharpened tip of the inner needle; and
a rod member hub for applying a force to move the rod member, and an engagement member for engaging the catheter hub and the rod member hub;
wherein the engagement member is an operation member, wherein the operation member is formed separately from the inner needle hub, is detachably attached to the catheter hub, is able to operate a movement of the catheter hub, and moves the rod member along with the movement of the catheter hub;

wherein, in a pre-puncture state of the catheter assembly, the sharpened tip of the inner needle protrudes from the distal end of the catheter and the blunt end of the rod member is disposed proximal to the sharpened tip inside the hollow portion of the inner needle, wherein the catheter and the rod member are moveable relative to the inner needle when moving from the pre-puncture state to a punctured state of the catheter assembly, when an engagement between the operation member and the rod member hub is disengaged during the movement by operating the operation member, the blunt end of the rod member is arranged so as to project from the sharpened tip, wherein, in the punctured state of the catheter assembly, the sharpened tip of the inner needle and the blunt end of the rod member are both disposed proximal to the distal end of the catheter inside the lumen, wherein the inner needle and the rod member are moveable relative to the catheter when moving from the punctured state to an indwelling state of the catheter assembly, wherein, in the indwelling state of the catheter assembly, the inner needle and the rod member are separated from the catheter and the blunt end of the rod member protrudes a distance from the sharpened tip of the inner needle, wherein the rod member hub comprises an engaging portion at a predetermined position, wherein the operation member comprises a portion to be engaged that engages with the engaging portion, wherein the portion to be engaged comprises a projection to be engaged, and wherein the projection to be engaged projects in a direction perpendicular to a moving direction of the operation member.

15. The catheter assembly of claim 14, wherein moving from the punctured state of the catheter assembly to the indwelling state of the catheter assembly comprises displacing the catheter a first distance in the distal direction, wherein the engagement between the operation member and the rod member hub is disengaged at a second distance shorter than the first distance, wherein at a point along the first distance and longer than the second distance the rod member hub is locked relative to the inner needle hub, and wherein movement of the catheter is physically separated from movement of the rod member hub.

16. The catheter assembly of claim 14, wherein the blunt end of the rod member is locked in a position relative to the inner needle such that the blunt end protrudes the distance from the sharpened tip of the inner needle.

17. The catheter assembly of claim 14, wherein the engaging portion comprises, in the pre-puncture state of the catheter assembly, a first engaging projection located on a distal end side of the projection to be engaged and capable of engaging the projection to be engaged.

18. The catheter assembly of claim 17, wherein the engaging portion further comprises a second engaging projection located on a proximal end side of the projection to be engaged and capable of engaging the projection to be engaged, and wherein the second engaging projection projects beyond the first engaging projection and, in a state where an engagement of the first engaging projection and the projection to be engaged is released, the projection to be engaged and the second engaging projection overlap in a front view of the catheter assembly.

* * * * *